US011697025B2

(12) United States Patent
Ghosh

(10) Patent No.: US 11,697,025 B2
(45) Date of Patent: Jul. 11, 2023

(54) CARDIAC CONDUCTION SYSTEM CAPTURE

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 415 days.

(21) Appl. No.: 16/370,203

(22) Filed: Mar. 29, 2019

(65) Prior Publication Data

US 2020/0306546 A1 Oct. 1, 2020

(51) Int. Cl.
| A61N 1/37 | (2006.01) |
| A61B 5/287 | (2021.01) |
| A61B 5/282 | (2021.01) |
| A61N 1/372 | (2006.01) |
| A61N 1/375 | (2006.01) |
| A61N 1/05 | (2006.01) |

(52) U.S. Cl.
CPC .............. *A61N 1/371* (2013.01); *A61B 5/282* (2021.01); *A61B 5/287* (2021.01); *A61N 1/372* (2013.01); *A61N 1/3714* (2013.01); *A61N 1/0573* (2013.01); *A61N 1/3756* (2013.01)

(58) Field of Classification Search
CPC .. A61N 1/3714; A61N 1/0565; A61N 1/0573; A61N 1/371; A61N 1/37205; A61N 1/3756; A61N 1/372; A61B 5/0422; A61B 5/282; A61B 5/287
See application file for complete search history.

(56) References Cited

U.S. PATENT DOCUMENTS

| 3,835,864 | A | 9/1974 | Rasor et al. |
| 3,865,118 | A | 2/1975 | Bures |
| 3,943,936 | A | 3/1976 | Rasor et al. |
| 3,949,757 | A | 4/1976 | Sabel |
| 4,142,530 | A | 3/1979 | Wittkampf |
| 4,151,513 | A | 4/1979 | Menken et al. |
| 4,157,720 | A | 6/1979 | Greatbatch |
| RE30,366 | E | 8/1980 | Rasor et al. |
| 4,233,987 | A | 11/1980 | Feingold |
| 4,243,045 | A | 1/1981 | Mass |
| 4,250,884 | A | 2/1981 | Hartlaub et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Pamela M. Bays
(74) *Attorney, Agent, or Firm* — Mueting Raasch Group

(57) ABSTRACT

Systems, methods, and devices are described herein for determining cardiac conduction system capture of ventricle from atrium (VfA) therapy. VfA therapy may be delivered at a plurality of different A-V delays while electrical activity of the patient is monitored. The electrical activity may then be utilized to determine whether the cardiac conduction system of the patient has been captured by the VfA therapy.

24 Claims, 13 Drawing Sheets

(56) References Cited

U.S. PATENT DOCUMENTS

| | | |
|---|---|---|
| 4,256,115 A | 3/1981 | Bilitch |
| 4,263,919 A | 4/1981 | Levin |
| 4,280,502 A | 7/1981 | Baker, Jr. et al. |
| 4,289,144 A | 9/1981 | Gilman |
| 4,310,000 A | 1/1982 | Lindemans |
| 4,312,354 A | 1/1982 | Walters |
| 4,323,081 A | 4/1982 | Wiebusch |
| 4,332,259 A | 6/1982 | McCorkle, Jr. |
| 4,357,946 A | 11/1982 | Dutcher et al. |
| 4,365,639 A | 12/1982 | Goldreyer |
| 4,374,382 A | 2/1983 | Markowitz et al. |
| 4,393,883 A | 7/1983 | Smyth et al. |
| 4,402,323 A | 9/1983 | White |
| 4,428,378 A | 1/1984 | Anderson et al. |
| 4,440,173 A | 4/1984 | Hudziak et al. |
| 4,476,868 A | 10/1984 | Thompson |
| 4,479,500 A | 10/1984 | Smits |
| 4,497,326 A | 2/1985 | Curry |
| 4,522,208 A | 6/1985 | Buffet |
| 4,537,200 A | 8/1985 | Widrow |
| 4,546,777 A | 10/1985 | Groch et al. |
| 4,556,063 A | 12/1985 | Thompson et al. |
| 4,562,841 A | 1/1986 | Brockway et al. |
| 4,566,456 A | 1/1986 | Koning et al. |
| 4,574,814 A | 3/1986 | Buffet |
| 4,593,702 A | 6/1986 | Kepski |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,674,511 A | 6/1987 | Cartmell |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,763,660 A | 8/1988 | Kroll et al. |
| 4,776,338 A | 10/1988 | Lekholm et al. |
| 4,777,955 A | 10/1988 | Brayten et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,865,037 A | 9/1989 | Chin et al. |
| 4,886,064 A | 12/1989 | Strandberg |
| 4,887,609 A | 12/1989 | Cole, Jr. |
| 4,928,688 A | 5/1990 | Mower |
| 4,953,564 A | 9/1990 | Berthelsen |
| 4,967,746 A | 11/1990 | Vandegriff |
| 4,979,507 A | 12/1990 | Heinz et al. |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,052,388 A | 10/1991 | Sivula et al. |
| 5,054,496 A | 10/1991 | Wen et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grievous et al. |
| 5,133,353 A | 7/1992 | Hauser |
| 5,144,950 A | 9/1992 | Stoop et al. |
| 5,154,170 A | 10/1992 | Bennett et al. |
| 5,170,784 A | 12/1992 | Ramon et al. |
| 5,174,289 A | 12/1992 | Cohen |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,692 A | 10/1993 | Neubauer et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,311,873 A | 5/1994 | Savard et al. |
| 5,312,439 A | 5/1994 | Loeb |
| 5,313,953 A | 5/1994 | Yomtov et al. |
| 5,314,459 A | 5/1994 | Swanson et al. |
| 5,318,594 A | 6/1994 | Limousin et al. |
| 5,318,597 A | 6/1994 | Hauck et al. |
| 5,324,316 A | 6/1994 | Schulman et al. |
| 5,331,960 A | 7/1994 | Lavine |
| 5,331,966 A | 7/1994 | Bennett et al. |
| 5,334,220 A | 8/1994 | Sholder |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,443,492 A | 8/1995 | Stokes et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,485,849 A | 1/1996 | Panescu et al. |
| 5,514,163 A | 5/1996 | Markowitz et al. |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,552,645 A | 9/1996 | Weng |
| 5,554,177 A | 9/1996 | Kieval et al. |
| 5,562,711 A | 10/1996 | Yerich et al. |
| 5,571,146 A | 11/1996 | Jones et al. |
| 5,591,214 A | 1/1997 | Lu |
| 5,601,615 A * | 2/1997 | Markowitz ............ A61N 1/368 607/28 |
| 5,620,466 A | 4/1997 | Haefner et al. |
| 5,628,778 A | 5/1997 | Kruse et al. |
| 5,634,938 A | 6/1997 | Swanson et al. |
| 5,649,968 A | 7/1997 | Alt et al. |
| 5,662,688 A | 9/1997 | Haefner et al. |
| 5,671,752 A | 9/1997 | Sinderby et al. |
| 5,674,259 A | 10/1997 | Gray |
| 5,683,426 A | 11/1997 | Greenhut et al. |
| 5,683,429 A | 11/1997 | Mehra |
| 5,683,432 A | 11/1997 | Goedeke et al. |
| 5,687,737 A | 11/1997 | Branham et al. |
| 5,706,823 A | 1/1998 | Wodlinger |
| 5,709,215 A | 1/1998 | Perttu et al. |
| 5,720,770 A | 2/1998 | Nappholz et al. |
| 5,728,140 A | 3/1998 | Salo et al. |
| 5,728,154 A | 3/1998 | Crossett et al. |
| 5,741,314 A | 4/1998 | Daly et al. |
| 5,741,315 A | 4/1998 | Lee et al. |
| 5,749,909 A | 5/1998 | Schroeppel et al. |
| 5,752,976 A | 5/1998 | Duffin et al. |
| 5,752,977 A | 5/1998 | Grievous et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,810,740 A | 9/1998 | Paisner |
| 5,814,089 A | 9/1998 | Stokes et al. |

(56) References Cited

U.S. PATENT DOCUMENTS

| | | | |
|---|---|---|---|
| 5,817,130 A | 10/1998 | Cox et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,876,336 A | 3/1999 | Swanson et al. |
| 5,891,045 A | 4/1999 | Albrecht et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,922,014 A | 7/1999 | Warman et al. |
| 5,928,271 A | 7/1999 | Hess et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,448 A | 4/2000 | Anderson et al. |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,128,535 A | 10/2000 | Maarse et al. |
| 6,132,456 A | 10/2000 | Sommer et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,187,032 B1 | 2/2001 | Ohyu et al. |
| 6,201,993 B1 | 3/2001 | Kruse et al. |
| 6,205,357 B1 | 3/2001 | Ideker et al. |
| 6,208,894 B1 | 3/2001 | Schulman et al. |
| 6,211,799 B1 | 4/2001 | Post et al. |
| 6,221,011 B1 | 4/2001 | Bardy |
| 6,226,542 B1 | 5/2001 | Reisfeld |
| 6,236,883 B1 | 5/2001 | Ciaccio et al. |
| 6,240,316 B1 | 5/2001 | Richmond et al. |
| 6,240,317 B1 | 5/2001 | Villaseca et al. |
| 6,243,603 B1 | 6/2001 | Ideker et al. |
| 6,246,898 B1 | 6/2001 | Vesely et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,903 B1 | 9/2001 | Rosenthal et al. |
| 6,285,907 B1 | 9/2001 | Kramer et al. |
| 6,285,908 B1 * | 9/2001 | Mann .................. A61N 1/3712 607/28 |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,301,496 B1 | 10/2001 | Reisfeld |
| 6,307,751 B1 | 10/2001 | Bodony et al. |
| 6,311,089 B1 | 10/2001 | Mann et al. |
| 6,312,378 B1 | 11/2001 | Bardy |
| 6,315,721 B2 | 11/2001 | Schulman et al. |
| 6,330,476 B1 | 12/2001 | Ben-Haim et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,358,214 B1 | 3/2002 | Tereschouk |
| 6,361,780 B1 | 3/2002 | Ley et al. |
| 6,368,284 B1 | 4/2002 | Bardy |
| 6,371,922 B1 | 4/2002 | Baumann et al. |
| 6,377,856 B1 | 4/2002 | Carson |
| 6,381,493 B1 | 4/2002 | Stadler et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,418,346 B1 | 7/2002 | Nelson et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,442,433 B1 | 8/2002 | Linberg |
| 6,443,891 B1 | 9/2002 | Grevious |
| 6,445,953 B1 | 9/2002 | Bulkes et al. |
| 6,453,200 B1 | 9/2002 | Koslar |
| 6,456,867 B2 | 9/2002 | Reisfeld |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,473,638 B2 | 10/2002 | Ferek-Petric |
| 6,480,745 B2 | 11/2002 | Nelson et al. |
| 6,484,118 B1 | 11/2002 | Govari |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,756 B1 | 1/2003 | Heynen et al. |
| 6,507,759 B1 | 1/2003 | Prutchi et al. |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,532,379 B2 | 3/2003 | Stratbucker |
| 6,539,253 B2 | 3/2003 | Thompson et al. |
| 6,542,775 B2 | 4/2003 | Ding et al. |
| 6,544,270 B1 | 4/2003 | Zhang |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,343 B1 | 6/2003 | Ransbury et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,599,250 B2 | 7/2003 | Webb et al. |
| 6,622,046 B2 | 9/2003 | Fraley et al. |
| 6,623,518 B2 | 9/2003 | Thompson et al. |
| 6,625,482 B1 | 9/2003 | Panescu et al. |
| 6,628,985 B2 | 9/2003 | Sweeney et al. |
| 6,640,136 B1 | 10/2003 | Helland et al. |

(56) References Cited

U.S. PATENT DOCUMENTS

| | | |
|---|---|---|
| 6,647,292 B1 | 11/2003 | Bardy et al. |
| 6,650,927 B1 | 11/2003 | Keidar |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,754,528 B2 | 6/2004 | Bardy et al. |
| 6,758,810 B2 | 7/2004 | Lebel et al. |
| 6,763,269 B2 | 7/2004 | Cox |
| 6,766,189 B2 | 7/2004 | Yu et al. |
| 6,772,004 B2 | 8/2004 | Rudy |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,555 B2 | 10/2004 | Warkentin |
| 6,804,558 B2 | 10/2004 | Haller et al. |
| 6,807,442 B1 | 10/2004 | Myklebust et al. |
| 6,847,836 B1 | 1/2005 | Sujdak |
| 6,847,844 B2 | 1/2005 | Sun et al. |
| 6,856,830 B2 | 2/2005 | He |
| 6,869,404 B2 | 3/2005 | Schulhauser et al. |
| 6,871,095 B2 | 3/2005 | Stahmann et al. |
| 6,871,096 B2 | 3/2005 | Hill |
| 6,878,112 B2 | 4/2005 | Linberg et al. |
| 6,882,882 B2 | 4/2005 | Struble et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,915,149 B2 | 7/2005 | Ben-Haim |
| 6,922,592 B2 | 7/2005 | Thompson et al. |
| 6,931,282 B2 | 8/2005 | Esler |
| 6,931,286 B2 | 8/2005 | Sigg et al. |
| 6,934,585 B1 | 8/2005 | Schloss et al. |
| 6,941,169 B2 | 9/2005 | Pappu |
| 6,957,107 B2 | 10/2005 | Rogers et al. |
| 6,968,237 B2 | 11/2005 | Doan et al. |
| 6,975,900 B2 | 12/2005 | Rudy et al. |
| 6,978,176 B2 | 12/2005 | Lattouf |
| 6,978,184 B1 | 12/2005 | Marcus et al. |
| 6,980,675 B2 | 12/2005 | Evron et al. |
| 6,985,773 B2 | 1/2006 | Von Arx et al. |
| 6,990,375 B2 | 1/2006 | Kloss et al. |
| 6,993,389 B2 | 1/2006 | Ding et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,176 B2 | 3/2006 | Ding et al. |
| 7,013,178 B2 | 3/2006 | Reinke et al. |
| 7,016,719 B2 | 3/2006 | Rudy et al. |
| 7,027,871 B2 | 4/2006 | Burnes et al. |
| 7,031,711 B2 | 4/2006 | Brown et al. |
| 7,031,771 B2 | 4/2006 | Brown et al. |
| 7,031,777 B2 | 4/2006 | Hine et al. |
| 7,035,684 B2 | 4/2006 | Lee et al. |
| 7,050,849 B2 | 5/2006 | Echt et al. |
| 7,058,443 B2 | 6/2006 | Struble |
| 7,060,031 B2 | 6/2006 | Webb et al. |
| 7,062,315 B2 | 6/2006 | Koyrakh et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,092,759 B2 | 8/2006 | Nehls et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,142,922 B2 | 11/2006 | Spinelli et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,284 B2 | 2/2007 | Burnes et al. |
| 7,181,505 B2 | 2/2007 | Haller et al. |
| 7,184,830 B2 | 2/2007 | Echt et al. |
| 7,184,835 B2 | 2/2007 | Kramer et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B2 | 5/2007 | Davis et al. |
| 7,212,871 B1 | 5/2007 | Morgan |
| 7,215,998 B2 | 5/2007 | Wesselink et al. |
| 7,226,440 B2 | 6/2007 | Gelfand et al. |
| 7,228,183 B2 | 6/2007 | Sun et al. |
| 7,231,248 B2 | 6/2007 | Kramer et al. |
| 7,231,253 B2 | 6/2007 | Tidemand et al. |
| 7,236,821 B2 | 6/2007 | Cates et al. |
| 7,236,829 B1 | 6/2007 | Farazi et al. |
| 7,238,158 B2 | 7/2007 | Abend |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,866 B2 | 10/2007 | Okerlund et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,307,321 B1 | 12/2007 | Avanzino |
| 7,308,297 B2 | 12/2007 | Reddy et al. |
| 7,308,299 B2 | 12/2007 | Burrell et al. |
| 7,310,556 B2 | 12/2007 | Bulkes |
| 7,313,444 B2 | 12/2007 | Pianca et al. |
| 7,317,950 B2 | 1/2008 | Lee |
| 7,319,905 B1 | 1/2008 | Morgan et al. |
| 7,321,677 B2 | 1/2008 | Evron et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,346,381 B2 | 3/2008 | Okerlund et al. |
| 7,346,393 B2 | 3/2008 | Spinelli et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,398,116 B2 | 7/2008 | Edwards |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,426,412 B1 | 9/2008 | Schecter |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,509,170 B2 | 3/2009 | Zhang et al. |
| 7,512,448 B2 | 3/2009 | Malick et al. |
| 7,515,969 B2 | 4/2009 | Tockman et al. |
| 7,526,342 B2 | 4/2009 | Chin et al. |

(56) References Cited

U.S. PATENT DOCUMENTS

| | | |
|---|---|---|
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,616,993 B2 | 11/2009 | Müssig et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,313 B2 | 2/2010 | Rom |
| 7,664,550 B2 | 2/2010 | Eick et al. |
| 7,668,596 B2 | 2/2010 | Von Arx et al. |
| 7,682,316 B2 | 3/2010 | Anderson et al. |
| 7,684,863 B2 | 3/2010 | Parikh et al. |
| 7,691,047 B2 | 4/2010 | Ferrari |
| 7,702,392 B2 | 4/2010 | Echt et al. |
| 7,706,879 B2 | 4/2010 | Burnes et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |
| 7,747,335 B2 | 6/2010 | Williams |
| 7,751,881 B2 | 7/2010 | Cowan et al. |
| 7,751,882 B1 | 7/2010 | Helland et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,451 B2 | 8/2010 | Yang et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,787,951 B1 | 8/2010 | Min |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,818,040 B2 | 10/2010 | Spear et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,807 B2 | 12/2010 | Wang |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,860,580 B2 | 12/2010 | Falk et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,889 B2 | 2/2011 | Zhang |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,917,214 B1 | 3/2011 | Gill et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,213 B2 | 5/2011 | Markowitz et al. |
| 7,941,214 B2 | 5/2011 | Kleckner et al. |
| 7,941,218 B2 | 5/2011 | Sambelashvili et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,475 B2 | 5/2011 | Harlev et al. |
| 7,953,482 B2 | 5/2011 | Hess |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,743 B2 | 7/2011 | Rudy et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,063 B2 | 8/2011 | Vass et al. |
| 7,996,070 B2 | 8/2011 | van Dam et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,194 B2 | 8/2011 | Muller |
| 8,010,209 B2 | 8/2011 | Jacobson |
| 8,014,861 B2 | 9/2011 | Zhu et al. |
| 8,019,402 B1 | 9/2011 | Kryzpow et al. |
| 8,019,409 B2 | 9/2011 | Rosenberg et al. |
| 8,019,419 B1 | 9/2011 | Panescu et al. |
| 8,019,434 B2 | 9/2011 | Quiles et al. |
| 8,027,727 B2 | 9/2011 | Freeberg |

(56) References Cited

U.S. PATENT DOCUMENTS

| | | |
|---|---|---|
| 8,027,729 B2 | 9/2011 | Sunagawa et al. |
| 8,032,219 B2 | 10/2011 | Neumann et al. |
| 8,032,229 B2 | 10/2011 | Gerber et al. |
| 8,036,743 B2 | 10/2011 | Savage et al. |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,145,308 B2 | 3/2012 | Sambelashvili et al. |
| 8,150,513 B2 | 4/2012 | Chinchoy |
| 8,150,521 B2 | 4/2012 | Crowley et al. |
| 8,160,672 B2 | 4/2012 | Kim et al. |
| 8,160,700 B1 | 4/2012 | Ryu et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,703 B2 | 5/2012 | Dong et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,292 B2 | 6/2012 | Rosenberg et al. |
| 8,195,293 B2 | 6/2012 | Limousin et al. |
| 8,204,590 B2 | 6/2012 | Sambelashvili et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,213,693 B1 | 7/2012 | Li |
| 8,214,041 B2 | 7/2012 | Van Gelder et al. |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,738 B1 | 9/2012 | Min et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,377 B2 | 10/2012 | Rosenberg et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,295,943 B2 | 10/2012 | Eggen et al. |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |
| 8,326,419 B2 | 12/2012 | Rosenberg et al. |
| 8,332,030 B2 | 12/2012 | Hess et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,308 B2 | 2/2013 | Rosenberg et al. |
| 8,380,320 B2 | 2/2013 | Spital |
| 8,383,269 B2 | 2/2013 | Scott et al. |
| 8,386,051 B2 | 2/2013 | Rys |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,716 B2 | 4/2013 | Mullen et al. |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,388 B2 | 7/2013 | Nguyen et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,896 B2 | 8/2013 | Doerr et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,051 B1 | 9/2013 | Hedberg et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matoes |
| 8,565,897 B2 | 10/2013 | Regnier et al. |
| 8,571,678 B2 | 10/2013 | Wang |
| 8,577,327 B2 | 11/2013 | Makdissi et al. |
| 8,583,230 B2 | 11/2013 | Ryu et al. |
| 8,588,926 B2 | 11/2013 | Moore et al. |
| 8,594,775 B2 | 11/2013 | Ghosh et al. |
| 8,612,002 B2 | 12/2013 | Faltys et al. |
| 8,615,298 B2 | 12/2013 | Ghosh et al. |
| 8,615,310 B2 | 12/2013 | Khairkhahan et al. |
| 8,617,082 B2 | 12/2013 | Zhang et al. |
| 8,620,433 B2 | 12/2013 | Ghosh et al. |
| 8,626,280 B2 | 1/2014 | Allavatam et al. |
| 8,626,294 B2 | 1/2014 | Sheldon et al. |
| 8,634,908 B2 | 1/2014 | Cowan |

(56) References Cited

U.S. PATENT DOCUMENTS

| | | |
|---|---|---|
| 8,634,912 B2 | 1/2014 | Bornzin et al. |
| 8,634,919 B1 | 1/2014 | Hou et al. |
| 8,639,333 B2 | 1/2014 | Stadler et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,314 B2 | 3/2014 | Maskara et al. |
| 8,676,319 B2 | 3/2014 | Knoll |
| 8,676,335 B2 | 3/2014 | Katoozi et al. |
| 8,694,099 B2 | 4/2014 | Ghosh et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,731,642 B2 | 5/2014 | Zarkh et al. |
| 8,738,132 B1 | 5/2014 | Ghosh et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,744,576 B2 | 6/2014 | Munsterman et al. |
| 8,747,314 B2 | 6/2014 | Stahmann et al. |
| 8,750,994 B2 | 6/2014 | Ghosh et al. |
| 8,750,998 B1 | 6/2014 | Ghosh et al. |
| 8,755,884 B2 | 6/2014 | Demmer et al. |
| 8,758,365 B2 | 6/2014 | Bonner et al. |
| 8,768,459 B2 | 7/2014 | Ghosh et al. |
| 8,768,465 B2 | 7/2014 | Ghosh et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,504 B2 | 8/2014 | Sweeney |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,861,830 B2 | 10/2014 | Brada et al. |
| 8,868,186 B2 | 10/2014 | Kroll |
| 8,886,307 B2 | 11/2014 | Sambelashvili et al. |
| 8,886,311 B2 | 11/2014 | Anderson et al. |
| 8,886,339 B2 | 11/2014 | Faltys et al. |
| 8,903,473 B2 | 12/2014 | Rogers et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,948,869 B2 | 2/2015 | Ghosh et al. |
| 8,948,883 B2 | 2/2015 | Eggen et al. |
| 8,958,892 B2 | 2/2015 | Khairkhahan et al. |
| 8,965,489 B2 | 2/2015 | Ghosh |
| 8,972,228 B2 | 3/2015 | Ghosh et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,031,642 B2 | 5/2015 | Ghosh |
| 9,033,996 B1 | 5/2015 | West |
| 9,037,238 B2 | 5/2015 | Stadler et al. |
| 9,037,262 B2 | 5/2015 | Regnier et al. |
| 9,042,984 B2 | 5/2015 | Demmer et al. |
| 9,072,872 B2 | 7/2015 | Asleson et al. |
| 9,072,911 B2 | 7/2015 | Hastings et al. |
| 9,072,913 B2 | 7/2015 | Jacobson |
| 9,101,281 B2 | 8/2015 | Reinert et al. |
| 9,119,959 B2 | 9/2015 | Rys et al. |
| 9,155,882 B2 | 10/2015 | Grubac et al. |
| 9,155,897 B2 | 10/2015 | Ghosh et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,199,087 B2 | 12/2015 | Stadler et al. |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,951 B2 | 2/2016 | Sweeney |
| 9,265,954 B2 | 2/2016 | Ghosh |
| 9,265,955 B2 | 2/2016 | Ghosh |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,219 B2 | 3/2016 | Ghosh |
| 9,278,220 B2 | 3/2016 | Ghosh |
| 9,278,229 B1 | 3/2016 | Reinke et al. |
| 9,282,907 B2 | 3/2016 | Ghosh |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,320,446 B2 | 4/2016 | Gillberg et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,474,457 B2 | 10/2016 | Ghosh et al. |
| 9,486,151 B2 | 11/2016 | Ghosh et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,510,763 B2 | 12/2016 | Ghosh et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,517,336 B2 | 12/2016 | Eggen et al. |
| 9,522,276 B2 | 12/2016 | Shen et al. |
| 9,522,280 B2 | 12/2016 | Fishler et al. |
| 9,526,435 B2 | 12/2016 | Ghosh |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |

(56) References Cited

U.S. PATENT DOCUMENTS

| | | |
|---|---|---|
| 9,566,012 B2 | 2/2017 | Greenhut et al. |
| 9,579,500 B2 | 2/2017 | Rys et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,603,651 B2 | 3/2017 | Ghosh |
| 9,610,045 B2 | 4/2017 | Du et al. |
| 9,623,234 B2 | 4/2017 | Anderson |
| 9,636,511 B2 | 5/2017 | Carney et al. |
| 9,643,014 B2 | 5/2017 | Zhang et al. |
| 9,675,579 B2 | 6/2017 | Rock et al. |
| 9,707,399 B2 | 7/2017 | Zielinski et al. |
| 9,724,519 B2 | 8/2017 | Demmer et al. |
| 9,737,223 B2 | 8/2017 | Du et al. |
| 9,750,941 B2 | 9/2017 | Ghosh |
| 9,764,143 B2 | 9/2017 | Ghosh et al. |
| 9,776,009 B2 | 10/2017 | Ghosh et al. |
| 9,782,094 B2 | 10/2017 | Du et al. |
| 9,789,319 B2 | 10/2017 | Sambelashvili |
| 9,808,628 B2 | 11/2017 | Sheldon et al. |
| 9,808,633 B2 | 11/2017 | Bonner et al. |
| 9,877,789 B2 | 1/2018 | Ghosh |
| 9,924,884 B2 | 3/2018 | Ghosh et al. |
| 9,974,457 B2 | 5/2018 | Ghosh et al. |
| 10,004,467 B2 | 6/2018 | Lahm et al. |
| 10,064,567 B2 | 9/2018 | Ghosh et al. |
| 10,099,050 B2 | 10/2018 | Chen et al. |
| 10,166,396 B2 | 1/2019 | Schrock et al. |
| 10,206,601 B2 | 2/2019 | Gillberg et al. |
| 10,251,555 B2 | 4/2019 | Ghosh et al. |
| 2002/0026220 A1* | 2/2002 | Groenewegen ........ A61B 5/322 607/4 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072682 A1 | 6/2002 | Hopman et al. |
| 2002/0072773 A1 | 6/2002 | Bardy et al. |
| 2002/0082665 A1 | 6/2002 | Haller et al. |
| 2002/0087089 A1 | 7/2002 | Ben-Haim |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2002/0173830 A1 | 11/2002 | Starkweather et al. |
| 2002/0193846 A1 | 12/2002 | Pool et al. |
| 2003/0004549 A1 | 1/2003 | Hill et al. |
| 2003/0009203 A1 | 1/2003 | Lebel et al. |
| 2003/0018277 A1 | 1/2003 | He |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0050670 A1 | 3/2003 | Spinelli et al. |
| 2003/0088278 A1 | 5/2003 | Bardy et al. |
| 2003/0092995 A1 | 5/2003 | Thompson |
| 2003/0097153 A1 | 5/2003 | Bardy et al. |
| 2003/0105495 A1 | 6/2003 | Yu et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2003/0236466 A1 | 12/2003 | Tarjan et al. |
| 2004/0015081 A1 | 1/2004 | Kramer et al. |
| 2004/0024435 A1 | 2/2004 | Leckrone et al. |
| 2004/0059237 A1 | 3/2004 | Narayan et al. |
| 2004/0064158 A1 | 4/2004 | Klein et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0097806 A1 | 5/2004 | Hunter et al. |
| 2004/0102812 A1 | 5/2004 | Yonce et al. |
| 2004/0102830 A1 | 5/2004 | Williams |
| 2004/0122479 A1 | 6/2004 | Spinelli et al. |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0162496 A1 | 8/2004 | Yu et al. |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172078 A1 | 9/2004 | Chinchoy |
| 2004/0172079 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0193223 A1 | 9/2004 | Kramer et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215245 A1 | 10/2004 | Stahmann et al. |
| 2004/0215252 A1 | 10/2004 | Verbeek et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220635 A1 | 11/2004 | Burnes |
| 2004/0220639 A1 | 11/2004 | Mulligan et al. |
| 2004/0230283 A1 | 12/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0090870 A1 | 4/2005 | Hine et al. |
| 2005/0096522 A1 | 5/2005 | Reddy et al. |
| 2005/0102003 A1 | 5/2005 | Grabek et al. |
| 2005/0107839 A1 | 5/2005 | Sanders |
| 2005/0137629 A1 | 6/2005 | Dyjach et al. |
| 2005/0137671 A1 | 6/2005 | Liu et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |

(56) References Cited

U.S. PATENT DOCUMENTS

| | | |
|---|---|---|
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161205 A1 | 7/2006 | Mitrani et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0224198 A1 | 10/2006 | Dong et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0253162 A1 | 11/2006 | Zhang et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049975 A1 | 3/2007 | Cates et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0142871 A1 | 6/2007 | Libbus et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0167809 A1 | 7/2007 | Dala-Krishna |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0232943 A1 | 10/2007 | Harel et al. |
| 2007/0233206 A1 | 10/2007 | Frikart et al. |
| 2007/0233216 A1 | 10/2007 | Liu et al. |
| 2007/0239244 A1 | 10/2007 | Morgan et al. |
| 2007/0250129 A1 | 10/2007 | Van Oort |
| 2007/0255376 A1 | 11/2007 | Michels et al. |
| 2007/0265508 A1 | 11/2007 | Sheikhzadeh-Nadjar et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021336 A1 | 1/2008 | Dobak et al. |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0027488 A1* | 1/2008 | Coles .................... A61N 1/056 607/9 |
| 2008/0058656 A1 | 3/2008 | Costello et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119903 A1 | 5/2008 | Arcot-Krishnamurthy et al. |
| 2008/0119911 A1 | 5/2008 | Rosero |
| 2008/0130670 A1 | 6/2008 | Kim et al. |
| 2008/0140143 A1 | 6/2008 | Ettori et al. |
| 2008/0146954 A1 | 6/2008 | Bojovic et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0242976 A1 | 10/2008 | Robertson et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269818 A1 | 10/2008 | Sullivan et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0281195 A1 | 11/2008 | Heimdal |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0048646 A1 | 2/2009 | Katoozi et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0084382 A1 | 4/2009 | Jalde et al. |
| 2009/0088813 A1 | 4/2009 | Brockway et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0171408 A1 | 7/2009 | Solem |
| 2009/0171414 A1 | 7/2009 | Kelly et al. |
| 2009/0198298 A1 | 8/2009 | Kaiser et al. |
| 2009/0204163 A1 | 8/2009 | Shuros et al. |
| 2009/0204170 A1 | 8/2009 | Hastings et al. |
| 2009/0210024 A1 | 8/2009 | Jason |
| 2009/0216112 A1 | 8/2009 | Assis et al. |
| 2009/0216292 A1 | 8/2009 | Pless et al. |
| 2009/0232448 A1 | 9/2009 | Barmash et al. |
| 2009/0234407 A1 | 9/2009 | Hastings et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0254140 A1 | 10/2009 | Rosenberg et al. |
| 2009/0266573 A1 | 10/2009 | Engmark et al. |
| 2009/0270729 A1 | 10/2009 | Corbucci et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299201 A1 | 12/2009 | Gunderson |
| 2009/0299423 A1 | 12/2009 | Min |
| 2009/0299447 A1 | 12/2009 | Jensen et al. |
| 2009/0306732 A1 | 12/2009 | Rosenberg et al. |
| 2009/0318995 A1 | 12/2009 | Keel et al. |
| 2010/0013668 A1 | 1/2010 | Kantervik |
| 2010/0016911 A1 | 1/2010 | Willis et al. |
| 2010/0016914 A1 | 1/2010 | Mullen et al. |
| 2010/0022873 A1 | 1/2010 | Hunter et al. |
| 2010/0023078 A1 | 1/2010 | Dong et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0049063 A1 | 2/2010 | Dobak, III |
| 2010/0063375 A1 | 3/2010 | Kassab et al. |
| 2010/0063562 A1 | 3/2010 | Cowan et al. |
| 2010/0065871 A1 | 3/2010 | Govari et al. |

(56) References Cited

U.S. PATENT DOCUMENTS

| | | |
|---|---|---|
| 2010/0069987 A1 | 3/2010 | Min et al. |
| 2010/0087888 A1 | 4/2010 | Maskara |
| 2010/0094149 A1 | 4/2010 | Kohut et al. |
| 2010/0094367 A1 | 4/2010 | Sen |
| 2010/0113954 A1 | 5/2010 | Zhou |
| 2010/0114209 A1 | 5/2010 | Krause et al. |
| 2010/0114214 A1 | 5/2010 | Morelli et al. |
| 2010/0114229 A1 | 5/2010 | Chinchoy |
| 2010/0121403 A1 | 5/2010 | Schecter et al. |
| 2010/0125281 A1 | 5/2010 | Jacobson et al. |
| 2010/0145405 A1 | 6/2010 | Min et al. |
| 2010/0152798 A1 | 6/2010 | Sanghera et al. |
| 2010/0168761 A1 | 7/2010 | Kassab et al. |
| 2010/0168819 A1 | 7/2010 | Freeberg |
| 2010/0174137 A1 | 7/2010 | Shim |
| 2010/0185250 A1 | 7/2010 | Rom |
| 2010/0198288 A1 | 8/2010 | Ostroff |
| 2010/0198291 A1 | 8/2010 | Sambelashvili et al. |
| 2010/0198292 A1 | 8/2010 | Honeck et al. |
| 2010/0198304 A1 | 8/2010 | Wang |
| 2010/0217367 A1 | 8/2010 | Belson |
| 2010/0218147 A1 | 8/2010 | Ishikawa |
| 2010/0228138 A1 | 9/2010 | Chen |
| 2010/0228308 A1 | 9/2010 | Cowan et al. |
| 2010/0234906 A1 | 9/2010 | Koh |
| 2010/0234916 A1 | 9/2010 | Turcott et al. |
| 2010/0234924 A1 | 9/2010 | Willis |
| 2010/0241185 A1 | 9/2010 | Mahapatra et al. |
| 2010/0249622 A1 | 9/2010 | Olson |
| 2010/0249729 A1 | 9/2010 | Morris et al. |
| 2010/0254583 A1 | 10/2010 | Chan et al. |
| 2010/0268059 A1 | 10/2010 | Ryu et al. |
| 2010/0286541 A1 | 11/2010 | Musley et al. |
| 2010/0286626 A1 | 11/2010 | Petersen |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0004111 A1 | 1/2011 | Gill et al. |
| 2011/0004264 A1 | 1/2011 | Siejko et al. |
| 2011/0022112 A1 | 1/2011 | Min |
| 2011/0022113 A1 | 1/2011 | Ideblick et al. |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0071586 A1 | 3/2011 | Jacobson |
| 2011/0075896 A1 | 3/2011 | Matsumoto |
| 2011/0077708 A1 | 3/2011 | Ostroff |
| 2011/0092809 A1 | 4/2011 | Nguyen et al. |
| 2011/0106202 A1 | 5/2011 | Ding et al. |
| 2011/0112398 A1 | 5/2011 | Zarkh et al. |
| 2011/0112600 A1 | 5/2011 | Cowan et al. |
| 2011/0118588 A1 | 5/2011 | Komblau et al. |
| 2011/0118803 A1 | 5/2011 | Hou et al. |
| 2011/0118810 A1 | 5/2011 | Cowan et al. |
| 2011/0137187 A1 | 6/2011 | Yang et al. |
| 2011/0137369 A1 | 6/2011 | Ryu et al. |
| 2011/0144510 A1 | 6/2011 | Ryu et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0172728 A1 | 7/2011 | Wang |
| 2011/0184297 A1 | 7/2011 | Vitali et al. |
| 2011/0184491 A1 | 7/2011 | Kivi |
| 2011/0190615 A1 | 8/2011 | Phillips et al. |
| 2011/0190835 A1 | 8/2011 | Brockway et al. |
| 2011/0190841 A1 | 8/2011 | Sambelashvili et al. |
| 2011/0196444 A1 | 8/2011 | Prakash et al. |
| 2011/0201915 A1 | 8/2011 | Gogin et al. |
| 2011/0208260 A1 | 8/2011 | Jacobson |
| 2011/0213260 A1 | 9/2011 | Keel et al. |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2011/0319954 A1 | 12/2011 | Niazi et al. |
| 2012/0004527 A1 | 1/2012 | Thompson et al. |
| 2012/0004567 A1 | 1/2012 | Eberle et al. |
| 2012/0029323 A1 | 2/2012 | Zhao |
| 2012/0035685 A1 | 2/2012 | Saha et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0089214 A1 | 4/2012 | Kroll et al. |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101543 A1 | 4/2012 | Demmer et al. |
| 2012/0101546 A1 | 4/2012 | Stadler et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109235 A1 | 5/2012 | Sheldon et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0203090 A1 | 8/2012 | Min |
| 2012/0215285 A1 | 8/2012 | Tahmasian et al. |
| 2012/0232478 A1 | 9/2012 | Haslinger |
| 2012/0232563 A1 | 9/2012 | Williams et al. |
| 2012/0232565 A1 | 9/2012 | Kveen et al. |
| 2012/0245665 A1 | 9/2012 | Friedman et al. |
| 2012/0253419 A1 | 10/2012 | Rosenberg et al. |
| 2012/0263218 A1 | 10/2012 | Dal Molin et al. |
| 2012/0277600 A1 | 11/2012 | Greenhut |
| 2012/0277606 A1 | 11/2012 | Ellingson et al. |
| 2012/0277725 A1 | 11/2012 | Kassab et al. |
| 2012/0283587 A1 | 11/2012 | Ghosh et al. |
| 2012/0283795 A1 | 11/2012 | Stancer et al. |
| 2012/0283807 A1 | 11/2012 | Deterre et al. |
| 2012/0284003 A1 | 11/2012 | Ghosh et al. |
| 2012/0290025 A1 | 11/2012 | Keimel |
| 2012/0296228 A1 | 11/2012 | Zhang et al. |
| 2012/0296381 A1 | 11/2012 | Matos |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303082 A1 | 11/2012 | Dong et al. |
| 2012/0303084 A1 | 11/2012 | Kleckner et al. |
| 2012/0310297 A1 | 12/2012 | Sweeney |
| 2012/0316613 A1 | 12/2012 | Keefe et al. |
| 2012/0330179 A1 | 12/2012 | Yuk et al. |
| 2013/0006332 A1 | 1/2013 | Sommer et al. |
| 2013/0012151 A1 | 1/2013 | Hankins |
| 2013/0013017 A1 | 1/2013 | Mullen et al. |
| 2013/0018250 A1 | 1/2013 | Caprio et al. |
| 2013/0018251 A1 | 1/2013 | Caprio et al. |
| 2013/0023975 A1 | 1/2013 | Locsin |
| 2013/0030491 A1 | 1/2013 | Stadler et al. |
| 2013/0035748 A1 | 2/2013 | Bonner et al. |

(56) References Cited

U.S. PATENT DOCUMENTS

| | | |
|---|---|---|
| 2013/0041422 A1 | 2/2013 | Jacobson |
| 2013/0053906 A1 | 2/2013 | Ghosh et al. |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0072790 A1 | 3/2013 | Ludwig et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096446 A1 | 4/2013 | Michael et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116739 A1 | 5/2013 | Brada et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131529 A1 | 5/2013 | Jia et al. |
| 2013/0131591 A1 | 5/2013 | Berthiaume et al. |
| 2013/0131693 A1 | 5/2013 | Berthiaume et al. |
| 2013/0131749 A1 | 5/2013 | Sheldon et al. |
| 2013/0131750 A1 | 5/2013 | Stadler et al. |
| 2013/0131751 A1 | 5/2013 | Stadler et al. |
| 2013/0136035 A1 | 5/2013 | Bange et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0184776 A1 | 7/2013 | Shuros et al. |
| 2013/0196703 A1 | 8/2013 | Masoud et al. |
| 2013/0197599 A1 | 8/2013 | Sambelashvili et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Walfhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261471 A1 | 10/2013 | Saha et al. |
| 2013/0261497 A1 | 10/2013 | Pertijs et al. |
| 2013/0261688 A1 | 10/2013 | Dong et al. |
| 2013/0265144 A1 | 10/2013 | Banna et al. |
| 2013/0268017 A1 | 10/2013 | Zhang et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0289640 A1 | 10/2013 | Zhang et al. |
| 2013/0138006 A1 | 11/2013 | Bornzin et al. |
| 2013/0296726 A1 | 11/2013 | Niebauer et al. |
| 2013/0296727 A1 | 11/2013 | Sullivan et al. |
| 2013/0303872 A1 | 11/2013 | Taff et al. |
| 2013/0304407 A1 | 11/2013 | George et al. |
| 2013/0324825 A1 | 12/2013 | Ostroff et al. |
| 2013/0324828 A1 | 12/2013 | Nishiwaki et al. |
| 2013/0325081 A1 | 12/2013 | Karst et al. |
| 2013/0345770 A1 | 12/2013 | Dianaty et al. |
| 2014/0005563 A1 | 1/2014 | Ramanathan et al. |
| 2014/0012344 A1 | 1/2014 | Hastings et al. |
| 2014/0018872 A1 | 1/2014 | Siejko et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0339570 A1 | 2/2014 | Carroll et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107507 A1 | 4/2014 | Ghosh et al. |
| 2014/0107723 A1* | 4/2014 | Hou ..................... A61N 1/3756 607/28 |
| 2014/0114173 A1 | 4/2014 | Bar-Tal et al. |
| 2014/0114372 A1 | 4/2014 | Ghosh et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0135866 A1 | 5/2014 | Ramanathan et al. |
| 2014/0135867 A1 | 5/2014 | Demmer et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163633 A1 | 6/2014 | Ghosh et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236252 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276125 A1 | 9/2014 | Hou et al. |
| 2014/0276929 A1 | 9/2014 | Foster et al. |
| 2014/0277233 A1 | 9/2014 | Ghosh |
| 2014/0303704 A1 | 10/2014 | Suwito et al. |
| 2014/0309706 A1 | 10/2014 | Jacobson |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0358135 A1 | 12/2014 | Sambelashvili et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2014/0379041 A1 | 12/2014 | Foster |
| 2015/0025612 A1 | 1/2015 | Haasl et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0039041 A1 | 2/2015 | Smith et al. |
| 2015/0045849 A1 | 2/2015 | Ghosh et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |

(56) References Cited

U.S. PATENT DOCUMENTS

| | | |
|---|---|---|
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Foster et al. |
| 2015/0105836 A1 | 4/2015 | Bonner et al. |
| 2015/0142069 A1 | 5/2015 | Sambelashvili |
| 2015/0142070 A1 | 5/2015 | Sambelashvili |
| 2015/0148697 A1 | 5/2015 | Burnes et al. |
| 2015/0149096 A1 | 5/2015 | Soykan |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157861 A1 | 6/2015 | Aghassian |
| 2015/0157865 A1 | 6/2015 | Gillberg et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0216434 A1 | 8/2015 | Ghosh et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0265840 A1 | 9/2015 | Ghosh et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0305695 A1 | 10/2015 | Lahm et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335894 A1 | 11/2015 | Bornzin et al. |
| 2016/0015287 A1 | 1/2016 | Anderson et al. |
| 2016/0015322 A1 | 1/2016 | Anderson et al. |
| 2016/0022164 A1 | 1/2016 | Brockway et al. |
| 2016/0023000 A1 | 1/2016 | Cho et al. |
| 2016/0030747 A1 | 2/2016 | Thakur et al. |
| 2016/0030751 A1 | 2/2016 | Ghosh et al. |
| 2016/0030757 A1 | 2/2016 | Jacobson |
| 2016/0033177 A1 | 2/2016 | Barot et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0051821 A1 | 2/2016 | Sambelashvili et al. |
| 2016/0059002 A1 | 3/2016 | Grubac et al. |
| 2016/0067486 A1 | 3/2016 | Brown et al. |
| 2016/0067487 A1 | 3/2016 | Demmer et al. |
| 2016/0067490 A1 | 3/2016 | Carney et al. |
| 2016/0114161 A1 | 4/2016 | Amblard et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129239 A1 | 5/2016 | Anderson |
| 2016/0184590 A1 | 6/2016 | Ghosh |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0310733 A1 | 10/2016 | Sheldon et al. |
| 2016/0317825 A1 | 11/2016 | Jacobson |
| 2016/0339248 A1 | 11/2016 | Schrock et al. |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056670 A1 | 3/2017 | Sheldon et al. |
| 2017/0182327 A1 | 6/2017 | Liu |
| 2017/0189681 A1 | 7/2017 | Anderson |
| 2017/0209689 A1 | 7/2017 | Chen |
| 2017/0216575 A1 | 8/2017 | Asleson et al. |
| 2017/0246460 A1 | 8/2017 | Ghosh |
| 2017/0246461 A1 | 8/2017 | Ghosh |
| 2017/0304624 A1 | 10/2017 | Friedman et al. |
| 2017/0326369 A1 | 11/2017 | Koop et al. |
| 2017/0340885 A1 | 11/2017 | Sambelashvili |
| 2018/0008829 A1 | 1/2018 | An et al. |
| 2018/0020938 A1 | 1/2018 | Du et al. |
| 2018/0021567 A1 | 1/2018 | An et al. |
| 2018/0021581 A1 | 1/2018 | An et al. |
| 2018/0021582 A1 | 1/2018 | An et al. |
| 2018/0050208 A1 | 2/2018 | Shuros et al. |
| 2018/0078773 A1 | 3/2018 | Thakur et al. |
| 2018/0078779 A1 | 3/2018 | An et al. |
| 2018/0117324 A1 | 5/2018 | Schilling et al. |
| 2018/0140847 A1 | 5/2018 | Taff et al. |
| 2018/0140848 A1 | 5/2018 | Stahmann |
| 2018/0178007 A1 | 6/2018 | Shuros et al. |
| 2018/0199843 A1 | 7/2018 | Ghosh et al. |
| 2018/0212451 A1 | 7/2018 | Schmidt et al. |
| 2018/0250514 A1 | 9/2018 | Ghosh |
| 2018/0263522 A1 | 9/2018 | Ghosh et al. |
| 2018/0264262 A1 | 9/2018 | Haasl et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0280686 A1 | 10/2018 | Shuros et al. |
| 2018/0303840 A1 | 10/2018 | Chopra et al. |
| 2018/0326215 A1 | 11/2018 | Ghosh |
| 2019/0030331 A1 | 1/2019 | Ghosh et al. |
| 2019/0030346 A1 | 1/2019 | Li |
| 2019/0038906 A1 | 2/2019 | Koop et al. |
| 2019/0083779 A1 | 3/2019 | Yang et al. |
| 2019/0083800 A1 | 3/2019 | Yang et al. |
| 2019/0083801 A1 | 3/2019 | Yang et al. |
| 2019/0143117 A1 | 5/2019 | Ghosh |
| 2019/0160288 A1 | 5/2019 | Stegemann et al. |
| 2019/0183370 A1 | 6/2019 | Gillberg et al. |
| 2019/0192023 A1 | 6/2019 | Ghosh |
| 2019/0192860 A1 | 6/2019 | Ghosh et al. |
| 2019/0269926 A1 | 9/2019 | Ghosh |
| 2019/0290909 A1* | 9/2019 | Ghosh ............... A61B 5/282 |

FOREIGN PATENT DOCUMENTS

| | | |
|---|---|---|
| AU | 2014203793 A1 | 7/2014 |
| CN | 1043621 A | 7/1990 |
| CN | 1253761 A | 5/2000 |
| CN | 1878595 A | 12/2006 |
| CN | 101073502 A | 11/2007 |
| CN | 202933393 | 5/2013 |
| EP | 0362611 A1 | 4/1990 |
| EP | 0459 239 A2 | 12/1991 |
| EP | 0 728 497 A2 | 8/1996 |
| EP | 1 072 284 A2 | 1/2001 |
| EP | 1 504 713 A1 | 2/2005 |
| EP | 1 541 191 A1 | 6/2005 |
| EP | 1 702 648 A1 | 9/2006 |
| EP | 2 016 976 A1 | 1/2009 |
| EP | 1 904 166 B1 | 6/2011 |
| EP | 2 391 270 A1 | 7/2011 |
| EP | 1 925 337 B1 | 3/2012 |
| EP | 2 436 309 A2 | 4/2012 |
| EP | 2 452 721 A1 | 5/2012 |
| EP | 2 471 452 A1 | 7/2012 |

(56) References Cited

FOREIGN PATENT DOCUMENTS

| EP | 2 435 132 B1 | 8/2013 |
|---|---|---|
| EP | 2 662 113 A2 | 11/2013 |
| EP | 1 703 944 B1 | 7/2015 |
| JP | 2005245215 | 9/2005 |
| WO | WO 95/00202 | 1/1995 |
| WO | WO 96/36134 | 11/1996 |
| WO | WO 97/24981 | 7/1997 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 02/22206 A1 | 3/2002 |
| WO | WO 2003/070323 A1 | 8/2003 |
| WO | WO 03/092800 A1 | 11/2003 |
| WO | WO 2005/000206 A2 | 1/2005 |
| WO | WO 2005/042089 A1 | 5/2005 |
| WO | WO 2005/056108 A2 | 6/2005 |
| WO | WO 2006/069215 A2 | 6/2006 |
| WO | WO 2006/086435 A2 | 8/2006 |
| WO | WO 2006/105474 A2 | 10/2006 |
| WO | WO 2006/113659 A1 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/073435 A1 | 6/2007 |
| WO | WO 2007/075974 A2 | 7/2007 |
| WO | WO 2007/139456 A1 | 12/2007 |
| WO | WO 2008/151077 A2 | 12/2008 |
| WO | WO 2009/006531 A1 | 1/2009 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2013/080038 A2 | 6/2013 |
| WO | WO 2013/098644 A2 | 7/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |
| WO | WO 2015/081221 A1 | 6/2015 |
| WO | WO 2016/011042 A1 | 1/2016 |
| WO | WO 2016/077099 A1 | 5/2016 |
| WO | WO 2016/110856 A1 | 7/2016 |
| WO | WO 2016/171891 A1 | 10/2016 |
| WO | WO 2017/075193 A1 | 5/2017 |
| WO | WO 2018/009569 A1 | 1/2018 |
| WO | WO 2018/017226 A1 | 1/2018 |
| WO | WO 2018/017361 A1 | 1/2018 |
| WO | WO 2018/035343 A1 | 2/2018 |
| WO | WO 2018/081519 A1 | 5/2018 |

OTHER PUBLICATIONS

International Search Report and Written Opinion from PCT Application No. PCT/US2020/019589 dated Jun. 4, 2020, 11 pages.
International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infarction" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.

(56) References Cited

OTHER PUBLICATIONS

Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010; pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.
Turner et al, "Electrical and Mechanical Components of Dyssynchrony in Heart Failure Patients with Normal QRS Duration and Left Bundle-Branch Block," *Circulation* 2004; 109:2544-2549.
Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," Annals of Biomedical Engineering, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
http://www.isrctn.com/ISRCTN47824547, public posting published Aug. 2019.
Abed et al., "Obesity results in progressive atrial structural and electrical remodeling: Implications for atrial fibrillation," *Heart Rhythm Society*, Jan. 2013; 10(1):90-100.
Adragão et al., "Ablation of pulmonary vein foci for the treatment of atrial fibrillation; percutaneous electroanatomical guided approach," *Europace*, Oct. 2002; 4(4):391-9.
Aliot et al., "Arrhythmia detection by dual-chamber implantable cardioverter defibrillators: A review of current algorithms," *Europace*, Jul. 2004; 6(4):273-86.
Amirahmadi et al., "Ventricular Tachycardia Caused by Mesothelial Cyst," *Indian Pacing and Electrophysiology Journal*, 2013; 13(1):43-44.

(56) References Cited

OTHER PUBLICATIONS

Ammirabile et al., "Pitx2 confers left morphological, molecular, and functional identity to the sinus venosus myocardium," *Cardiovasc Res.*, Feb. 2012; 93(2):291-301.
Anfinsen, "Non-pharmacological Treatment of Atrial Fibrillation," *Indian Pacing and Electrophysiology Journal*, Jan. 2002; 2(1):4-14.
Anné et al., "Ablation of post-surgical intra-atrial reentrant Tachycardia," *European Heart Journal*, 2002; 23:169-1616.
Arenal et al., "Dominant frequency differences in atrial fibrillation patients with and without left ventricular systolic dysfunction," *Europace*, Apr. 2009; 11(4):450-457.
Arriagada et al., "Predictors of arrhythmia recurrence in patients with lone atrial fibrillation," *Europace*, Jan. 2008; 10(1):9-14.
Asirvatham et al., "Cardiac Anatomic Considerations in Pediatric Electrophysiology," *Indian Pacing and Electrophysiology Journal*, Apr. 2008; 8(Suppl 1):S75-S91.
Asirvatham et al., "Intramyocardial Pacing and Sensing for the Enhancement of Cardiac Stimulation and Sensing Specificity," *Pacing Clin. Electrophysiol.*, Jun. 2007; 30(6):748-754.
Asirvatham et al., "Letter to the Editor," *J Cardiovasc Electrophysiol.*, Mar. 2010; 21(3): E77.
Balmer et al., "Long-term follow up of children with congenital complete atrioventricular block and the impact of pacemaker therapy," *Europace*, Oct. 2002; 4(4):345-349.
Barold et al., "Conventional and biventricular pacing in patients with first-degree atrioventricular block," *Europace*, Oct. 2012; 14(10):1414-9.
Barold et al., "The effect of hyperkalaemia on cardiac rhythm devices," *Europace*, Apr. 2014; 16(4):467-76.
Bayrak et al., "Added value of transoesophageal echocardiography during transseptal puncture performed by inexperienced operators," *Europace*, May 2012; 14(5):661-5.
Bergau et al., "Measurement of Left Atrial Pressure is a Good Predictor of Freedom From Atrial Fibrillation," *Indian Pacing and Electrophysiology Journal*, Jul. 2014; 14(4):181-93.
Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.
Bito et al., "Early exercise training after myocardial infarction prevents contractile but not electrical remodeling or hypertrophy," *Cardiovascular Research*, Apr. 2010; 86(1):72-81.
Bollmann et al., "Analysis of surface electrocardiograms in atrial fibrillation: techniques, research, and clinical applications," *Europace*, Nov. 2006; 8(11):911-926.
Bortone et al., "Evidence for an incomplete mitral isthmus block after failed ablation of a left postero-inferior concealed accessory pathway," *Europace*, Jun. 2006; 8(6):434-7.
Boulos et al., "Electroanatomical mapping and radiofrequency ablation of an accessory pathway associated with a large aneurysm of the coronary sinus," *Europace*, Nov. 2004; 6(6):608-12.
Brembilla-Perrot et al., "Incidence and prognostic significance of spontaneous and inducible antidromic tachycardia," *Europace*, Jun. 2013; 15(6):871-876.
Buber et al., "Morphological features of the P-waves at surface electrocardiogram as surrogate to mechanical function of the left atrium following a successful modified maze procedure," *Europace*, Apr. 2014; 16(4):578-86.
Burashnikov et al., "Late-phase 3 EAD. A unique mechanism contributing to initiation of atrial fibrillation," *Pacing Clin Electrophysiol.*, Mar. 2006; 29(3):290-5.
Burashnikov et al., "Atrial-selective inhibition of sodium-channel current by Wenxin Keli is effective in suppressing atrial fibrillation," *Heart Rhythm*, Jan. 2012; 9(1):125-31.
Calvo et al., "Efficacy of circumferential pulmonary vein ablation of atrial fibrillation in endurance athletes," *Europace*, Jan. 2010; 12(1):30-6.

Can et al., ""Atrial torsades de pointes" Induced by Low-Energy Shock From Implantable-Cardioverter Defibrillator," *Indian Pacing and Electrophysiology Journal*, Sep. 2013; 13(5):194-199.
Carroz et al., "Pseudo-pacemaker syndrome in a young woman with first-degree atrio-ventricular block," *Europace*, Apr. 2010; 12(4):594-596.
Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3):227-233.
Cazeau et al., "Cardiac resynchronization therapy," *Europace*, Sep. 2004; 5 Suppl 1:S42-8.
Chandra et al., "Evaluation of KCB-328, a new IKr blocking antiarrhythmic agent in pacing induced canine atrial fibrillation," *Europace*, Sep. 2004; 6(5):384-91.
Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013; 13(4):142-7.
Climent et al., "Effects of endocardial microwave energy ablation," *Indian Pacing and Electrophysiology Journal*, Jul. 2005; 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*,1998, 193:105-119.
Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary syndrome," *Indian Pacing and Electrophysiology Journal*, Jan. 2012; 12(1):19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005; 28(7):639-46.
Dizon et al. "Real-time stroke vol. measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *Pace*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1):70-4.

(56) References Cited

OTHER PUBLICATIONS

Frogoudaki et al., "Pacing for adult patients with left atrial isomerism: efficacy and technical considerations," *Europace*, Apr. 2003; 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12):1630-40.
Geddes, "Accuracy limitations of chronaxie values," *IEEE Trans Biomed Eng.*, Jan. 2004; 51(1):176-81.
Gertz et al., "The impact of mitral regurgitation on patients undergoing catheter ablation of atrial fibrillation," *Europace*, Aug. 2011; 13(8):1127-32.
Girmatsion et al., "Changes in microRNA-1 expression and IK1 up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010; 85(1):45-55.
Guenther et al., "Substernal Lead Implantation: A Novel Option to Manage OFT Failure in S-ICD patients," *Clinical Research Cardiology*, Feb. 2015; Epub Oct. 2, 2014; 104(2):189-91.
Guillem et al., "Noninvasive mapping of human atrial fibrillation," *J Cardiovasc Electrophysiol.*, May 2009; 20(5):507-513.
Hachisuka et al., "Development and Performance Analysis of an Intra-Body Communication Device," *The 12$^{th}$ International Conference on Solid State Sensors, Actuators and Microsystems*, vol. 4A1.3, pp. 1722-1725, 2003.
Hakacova et al., "Septal atrial pacing for the prevention of atrial fibrillation," *Europace*, 2007; 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.
Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.
He et al., "Three-dimensional cardiac electrical imaging from intracavity recordings," *IEEE Trans Biomed Eng.*, Aug. 2007; 54(8):1454-60.
Heist et al., "Direct visualization of epicardial structures and ablation utilizing a visually guided laser balloon catheter: preliminary findings," *J Cardiovasc Electrophysiol.*, Jul. 2011; 22(7):808-12.
Henz et al., "Synchronous Ventricular Pacing without Crossing the Tricuspid Valve or Entering the Coronary Sinus—Preliminary Results," *J Cardiovasc Electrophysiol.*, Dec. 2009; 20(12):1391-1397.
Hiippala et al., "Automatic Atrial Threshold Measurement and Adjustment in Pediatric Patients," *Pacing Clin Electrophysiol.*, Mar. 2010; 33(3):309-13.
Ho, "Letter to the Editor" *J Cardiovasc Electrophysiol.*, Mar. 2010; 21(3): E76.
Höijer et al., "Improved cardiac function and quality of life following upgrade to dual chamber pacing after long-term ventricular stimulation," *European Heart Journal*, Mar. 2002; 23(6):490-497.
Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.

Inter-Office Memo, Model 6426-85 Canine Feasibility AV Septal 8 mm Screw-In Right Single Pass DDD Lead Final Report (AR # 0120A0207).
Ishigaki et al., "Prevention of immediate recurrence of atrial fibrillation with low-dose landiolol after radiofrequency catheter ablation," *Journal of Arrhythmia*, Oct. 2015; 31(5):279-285.
Israel, "The role of pacing mode in the development of atrial fibrillation," *Europace*, Feb. 2006; 8(2):89-95.
Janion et al., "Dispersion of P wave duration and P wave vector in patients with atrial septal aneurysm," *Europace*, Jul. 2007; 9(7):471-4.
Kabra et al., "Recent Trends in Imaging for Atrial Fibrillation Ablation," *Indian Pacing and Electrophysiology Journal*, 2010; 10(5):215-227.
Kalbfleisch et al., "Catheter Ablation with Radiofrequency Energy: Biophysical Aspects and Clinical Applications," *Journal of Cardiovascular Electrophysiology*, Oct. 2008; 3(2):173-186.
Katritsis et al., "Classification and differential diagnosis of atrioventricular nodal re-entrant tachycardia," *Europace*, Jan. 2006; 8(1):29-36.
Katritsis et al., "Anatomically left-sided septal slow pathway ablation in dextrocardia and situs inversus totalis," *Europace*, Aug. 2008; 10(8):1004-5.
Khairy et al., "Cardiac Arrhythmias in Congenital Heart Diseases," *Indian Pacing and Electrophysiology Journal*, Nov.-Dec. 2009; 9(6):299-317.
Kimmel et al., "Single-site ventricular and biventricular pacing: investigation of latest depolarization strategy," *Europace*, Dec. 2007; 9(12):1163-1170.
Knackstedt et al., "Electro-anatomic mapping systems in arrhythmias," *Europace*, Nov. 2008; 10 Suppl 3:iii28-iii34.
Kobayashi et al., "Successful Ablation of Antero-septal Accessory Pathway in the Non-Coronary Cusp in a Child," *Indian Pacing and Electrophysiology Journal*, 2012; 12(3):124-130.
Kojodjojo et al., "4:2:1 conduction of an AF initiating trigger," *Indian Pacing and Electrophysiology Journal*, Nov. 2015; 15(5):255-8.
Kołodzińska et al., "Differences in encapsulating lead tissue in patients who underwent transvenous lead removal," *Europace*, Jul. 2012; 14(7):994-1001.
Konecny et al., "Synchronous intra-myocardial ventricular pacing without crossing the tricuspid valve or entering the coronary sinus," *Cardiovascular Revascularization Medicine*, 2013; 14:137-138.
Kriatselis et al., "Ectopic atrial tachycardias with early activation at His site: radiofrequency ablation through a retrograde approach," *Europace*, Jun. 2008; 10(6):698-704.
Lalu et al., "Ischaemia-reperfusion injury activates matrix metalloproteinases in the human heart," *Eur Heart J.*, Jan. 2005; 26(1):27-35.
Laske et al., "Excitation of the Intrinsic Conduction System Through His and Interventricular Septal Pacing," *Pacing Clin. Electrophysiol.*, Apr. 2006; 29(4):397-405.
Leclercq, "Problems and troubleshooting in regular follow-up of patients with cardiac resynchronization therapy," *Europace*, Nov. 2009; 11 Suppl 5:v66-71.
Lee et al., "An unusual atrial tachycardia in a patient with Friedreich ataxia," *Europace*, Nov. 2011; 13(11):1660-1.
Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.
Lemay et al., "Spatial dynamics of atrial activity assessed by the vectorcardiogram: from sinus rhythm to atrial fibrillation," *Europace*, Nov. 2007; 9 Suppl 6:vi109-18.
Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.
Lewalter et al., "Comparison of spontaneous atrial fibrillation electrogram potentials to the P wave electrogram amplitude in dual chamber pacing with unipolar atrial sensing," *Europace*, Apr. 2000; 2(2):136-40.

(56) References Cited

OTHER PUBLICATIONS

Liakopoulos et al., "Sequential deformation and physiological considerations in unipolar right and left ventricular pacing," *European Journal of Cardio-thoracic Surgery*, Apr. 1, 2006; 29S1:S188-197.
Lian et al., "Computer modeling of ventricular rhythm during atrial fibrillation and ventricular pacing," *IEEE Transactions on Biomedical Engineering*, Aug. 2006; 53(8):1512-1520.
Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.
Lim et al., "Coupled pacing improves left ventricular function during simulated atrial fibrillation without mechanical dyssynchrony," *Europace*, Mar. 2010; 12(3):430-6.
Lou et al., "Tachy-brady arrhythmias: The critical role of adenosine-induced sinoatrial conduction block in post-tachycardia pauses," *Heart Rhythm.*, Jan. 2013; 10(1):110-8.
Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.
Macedo et al, "Septal accessory pathway: anatomy, causes for difficulty, and an approach to ablation," *Indian Pacing and Electrophysiology Journal*, Jul. 2010; 10(7):292-309.
Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.
Mani et al., "Dual Atrioventricular Nodal Pathways Physiology: A Review of Relevant Anatomy, Electrophysiology, and Electrocardiographic Manifestations," *Indian Pacing and Electrophysiology Journal*, Jan. 2014; 14(1):12-25.
Manios et al., "Effects of successful cardioversion of persistent atrial fibrillation on right ventricular refractoriness and repolarization," *Europace*, Jan. 2005; 7(1):34-9.
Manolis et al., "Prevention of atrial fibrillation by inter-atrial septum pacing guided by electrophysiological testing, in patients with delayed interatrial conduction," *Europace*, Apr. 2002; 4(2):165-174.
Marino et al., "Inappropriate mode switching clarified by using a chest radiograph," *Journal of Arrhythmia*, Aug. 2015; 31(4):246-248.
Markowitz et al., "Time course and predictors of autonomic dysfunction after ablation of the slow atrioventricular nodal pathway," *Pacing Clin Electrophysiol.*, Dec. 2004; 27(12):1638-43.
Marshall et al., "The effects of temperature on cardiac pacing thresholds," *Pacing Clin Electrophysiol.*, Jul. 2010; 33(7):826-833.
McSharry et al., "A Dynamical Model for Generating Synthetic Electrocardiogram Signals," *IEEE Transactions on Biomedical Engineering*, Mar. 2003; 50(3):289-294.
Meijler et al., "Scaling of Atrioventricular Transmission in Mammalian Species: An Evolutionary Riddle!," *Journal of Cfardiovascular Electrophysiology*, Aug. 2002; 13(8):826-830.
Meiltz et al., "Permanent form of junctional reciprocating tachycardia in adults: peculiar features and results of radiofrequency catheter ablation," *Europace*, Jan. 2006; 8(1):21-8.
Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.
Mestan et al., "The influence of fluid and diuretic administration on the index of atrial contribution in sequentially paced patients," *Europace*, Apr. 2006; 8(4):273-8.
Metin et al., "Assessment of the P Wave Dispersion and Duration in Elite Women Basketball Players," *Indian Pacing and Electrophysiology Journal*, 2010; 10(1):11-20.
Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009; 2(5):571-579.

Mitchell et al., "How do atrial pacing algorithms prevent atrial arrhythmias?" *Europace*, Jul. 2004; 6(4):351-62.
Mirzoyev et al., "Embryology of the Conduction System for the Electrophysiologist," *Indian Pacing and Electrophysiology Journal*, 2010; 10(8):329-338.
Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.
Montgomery et al., "Measurement of diffuse ventricular fibrosis with myocardial T1 in patients with atrial fibrillation," *J Arrhythm.*, Feb. 2016; 32(1):51-6.
Mulpuru et al., "Synchronous ventricular pacing with direct capture of the atrioventricular conduction system: Functional anatomy, terminology, and challenges," *Heart Rhythm*, Nov. 2016; Epub Aug. 3, 2016; 13(11):2237-2246.
Musa et al, "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7):1044-1051.
Nagy et al., "Wnt-11 signalling controls ventricular myocardium development by patterning N-cadherin and β-catenin expression," *Cardiovascular Research*, Jan. 2010; 85(1):100-9.
Namboodiri et al., "Electrophysiological features of atrial flutter in cardiac sarcoidosis: a report of two cases," *Indian Pacing and Electrophysiology Journal*, Nov. 2012; 12(6):284-9.
Nanthakumar et al., "Assessment of accessory pathway and atrial refractoriness by transesophageal and intracardiac atrial stimulation: An analysis of methodological agreement," *Europace*, Jan. 1999; 1(1):55-62.
Neto et al., "Temporary atrial pacing in the prevention of postoperative atrial fibrillation," *Pacing Clin Electrophysiol.*, Jan. 2007; 30(Suppl 1):S79-83.
Nishijima et al., "Tetrahydrobiopterin depletion and NOS2 uncoupling contribute to heart failure-induced alterations in atrial electrophysiology," *Cardiovasc Res.*, Jul. 2011; 91(1):71-9.
Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.
Okumura et al., "Effects of a high-fat diet on the electrical properties of porcine atria," *Journal of Arrhythmia*, Dec. 2015; 31(6):352-358.
Olesen et al., "Mutations in sodium channel β-subunit SCN3B are associated with early-onset lone atrial fibrillation," *Cardiovascular Research*, Mar. 2011; 89(4):786-93.
Ozmen et al., "P wave dispersion is increased in pulmonary stenosis," *Indian Pacing and Electrophysiology Journal*, Jan. 2006; 6(1):25-30.
Packer et al., "New generation of electro-anatomic mapping: Full intracardiac image integration," *Europace*, Nov. 2008; 10 Suppl 3:iii35-41.
Page et al., "Ischemic ventricular tachycardia presenting as a narrow complex tachycardia," *Indian Pacing and Electrophysiology Journal*, Jul. 2014; 14(4):203-210.
Pakarinen et al., "Pre-implant determinants of adequate long-term function of single lead VDD pacemakers," *Europace*, Apr. 2002; 4:137-141.
Patel et al., "Atrial Fibrillation after Cardiac Surgery: Where are we now?" *Indian Pacing and Electrophysiology Journal*, Oct.-Dec. 2008; 8(4):281-291.
Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.
Peschar et al., "Left Ventricular Septal and Apex Pacing for Optimal Pump Function in Canine Hearts," *J Am Coll Cardiol.*, Apr. 2, 2003; 41(7):1218-1226.
Physiological Research Laboratories, Final Report for an Acute Study for Model 6426-85 AV Septal Leads, Feb. 1996.
Porciani et al., "Interatrial septum pacing avoids the adverse effect of interatrial delay in biventricular pacing: an echo-Doppler evaluation," *Europace*, Jul. 2002; 4(3):317-324.

(56) References Cited

OTHER PUBLICATIONS

Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.
Prystowsky et al., "Case studies with the experts: management decisions in atrial fibrillation," *J Cardiovasc Electrophysiol.*, Feb. 2008; 19(Suppl. 1):S1-12.
Prystowsky, "The history of atrial fibrillation: the last 100 years," *J Cardiovasc Electrophysiol*, Jun. 2008; 19(6):575-582.
Pytkowski et al., "Paroxysmal atrial fibrillation is associated with increased intra-atrial conduction delay," *Europace*, Dec. 2008; 10(12):1415-20.
Qu et al., "Dynamics and cardiac arrhythmias," *J Cardiovasc Electrophysiol.*, Sep. 2006; 17(9):1042-9.
Ravens et al., "Role of potassium currents in cardiac arrhythmias," *Europace*, Oct. 2008; 10(10):1133-7.
Ricci et al., Efficacy of a dual chamber defibrillator with atrial antitachycardia functions in treating spontaneous atrial tachyarrhythmias in patients with life-threatening ventricular tachyarrhythmias, *European Heart Journal*, Sep. 2002; 23(18):1471-9.
Roberts-Thomson et al., "Focal atrial tachycardia II: management," *Pacing Clin Electrophysiol.*, Jul. 2006; 29(7):769-78.
Rossi et al., "Endocardial vagal atrioventricular node stimulation in humans: reproducibility on 18-month follow-up," *Europace*, Dec. 2010; 12(12):1719-24.
Rouzet et al., "Contraction delay of the RV outflow tract in patients with Brugada syndrome is dependent on the spontaneous ST-segment elevation pattern," *Heart Rhythm*, Dec. 2011; 8(12):1905-12.
Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.
Sairaku et al., "Prediction of sinus node dysfunction in patients with persistent atrial flutter using the flutter cycle length," *Europace*, Mar. 2012; 14(3):380-7.
Santini et al., "Immediate and long-term atrial sensing stability in single-lead VDD pacing depends on right atrial dimensions," *Europace*, Oct. 2001; 3(4):324-31.
Saremi et al., "Cardiac Conduction System: Delineation of Anatomic Landmarks With Multidetector CT," *Indian Pacing and Electrophysiology Journal*, Nov. 2009; 9(6):318-33.
Savelieva et al., "Anti-arrhythmic drug therapy for atrial fibrillation: current anti-arrhythmic drugs, investigational agents, and innovative approaches," *Europace*, Jun. 2008; 10(6):647-665.
Schmidt et al., "Navigated Dense strain imaging for post-radiofrequency ablation lesion assessment in the swine left atria," *Europace*, Jan. 2014; 16(1):133-41.
Schoonderwoerd et al., "Rapid Pacing Results in Changes in Atrial but not in Ventricular Refractoriness," *Pacing Clin Electrophysiol.*, Mar. 2002; 25(3):287-90.
Schoonderwoerd et al., "Atrial natriuretic peptides during experimental atrial tachycardia: role of developing tachycardiomyopathy," *J Cardiovasc Electrophysiol.*, Aug. 2004; 15(8):927-32.
Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body Area Network Application," *IEEE Transactions on Biomedical Engineering*, vol. 60(8): 2067-2079, 2013.
Shah et al., "Stable atrial sensing on long-term follow up of VDD pacemakers," *Indian Pacing and Electrophysiology Journal*, Oct. 2006; 6(4):189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.
Shenthar et al., "Transvenous permanent pacemaker implantation in dextrocardia: technique, challenges, outcome, and a brief review of literature," *Europace*, Sep. 2014; 16(9):1327-33.
Shirayama, "Role of atrial fibrillation threshold evaluation on guiding treatment," *Indian Pacing and Electrophysiology Journal*, Oct. 2003; 3(4):224-230.
Spickler et al., "Totally Self-Contained Intracardiac Pacemaker," Journal of Electrocardiology, vol. 3(3&4): 324-331, 1970.
Sreeram et al., "Indications for Electrophysiology Study in children," *Indian Pacing and Electrophysiology Journal*, Apr.-Jun. 2008; 8(Suppl. 1):S36-S54.
Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.
Stroobandt et al., "Prediction of Wenckebach Behavior and Block Response in DDD Pacemakers," *Pacing Clin Electrophysiol.*, Jun. 2006; 9(6):1040-6.
Suenari et al., "Idiopathic left ventricular tachycardia with dual electrocardiogram morphologies in a single patient," *Europace*, Apr. 2010; 12(4):592-4.
Sweeney et al., "Analysis of Ventricular Activation Using Surface Electrocardiography to Predict Left Ventricular Reverse Volumetric Remodeling During Cardiac Resynchronization Therapy," Circulation, Feb. 9, 2010, 121(5): 626-34.
Tan et al., "Electrocardiographic evidence of ventricular repolarization remodelling during atrial fibrillation," *Europace*, Jan. 2008; 10(1):99-104.
Taramasco et al., "Internal low-energy cardioversion: a therapeutic option for restoring sinus rhythm in chronic atrial fibrillation after failure of external cardioversion," *Europace*, Jul. 1999; 1(3):179-82.
Testa et al., "Rate-control or rhythm-control: where do we stand?" *Indian Pacing and Electrophysiology Journal*, Oct. 2005; 5(4):296-304.
Thejus et al., "N-terminal Pro-Brain Natriuretic Peptide and Atrial Fibrillation," *Indian Pacing and Electrophysiology Journal*, Jan. 2009; 9(1):1-4.
Thornton et al., "Magnetic Assisted Navigation in Electrophysiology and Cardiac Resynchronisation: A Review," *Indian Pacing and Electrophysiology Journal*, Oct. 2006; 6(4):202-13.
Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.
Tomaske et al., "Do daily threshold trend fluctuations of epicardial leads correlate with pacing and sensing characteristics in paediatric patients?" *Europace*, Aug. 2007, 9(8):662-668.
Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.
Tournoux et al., "A 'Regularly Irregular' tachycardia: What is the diagnosis?" *Europace*, Dec. 2008; 10(12):1445-6.
Traykov et al., "Electrogram analysis at the His bundle region and the proximal coronary sinus as a tool to predict left atrial origin of focal atrial tachycardias," *Europace*, Jul. 2011; 13(7):1022-7.
Trudel et al., "Simulation of QRST integral maps with a membrane-based computer heart model employing parallel processing," *IEEE Trans Biomed Eng.*, Aug. 2004; 51(8):1319-29.
Tse et al., "Cardiac dynamics: Alternans and arrhythmogenesis," *Journal of Arrhythmia*, Oct. 2016; 32(5):411-417.
Tse, "Mechanisms of cardiac arrhythmias," *Journal of Arrhythmia*, Apr. 2016; 32(2):75-81.
Ueda et al., "Outcomes of single- or dual-chamber implantable cardioverter defibrillator systems in Japanese patients," *Journal of Arrhythmia*, Apr. 2016; 32(2):89-94.
Van Dam et al., "Volume conductor effects involved in the genesis of the P wave," *Europace*, Sep. 2005; 7 Suppl 2:30-8.
Van den Berg et al., "Depletion of atrial natriuretic peptide during longstanding atrial fibrillation," *Europace*, Sep. 2004; 6(5):433-7.

(56) References Cited

OTHER PUBLICATIONS

Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.
Van Opstal et al., "Paradoxical increase of stimulus to atrium interval despite His-bundle capture during para-Hisian pacing," *Europace*, Dec. 2009; 11(12):1702-4.
Veenhuyzen et al., "Diagnostic pacing maneuvers for supraventricular tachycardia: part 1," *Pacing Clin Electrophysiol.*, Jun. 2011; 34(6):767-82.
Veenhuyzen et al., "Diagnostic pacing maneuvers for supraventricular tachycardias: part 2," *Pacing Clin Electrophysiol.*, Jun. 2012; 35(6):757-69.
Veenhuyzen et al., "Principles of Entrainment: Diagnostic Utility for Supraventricular Tachycardia," *Indian Pacing and Electrophysiology Journal*, 2008; 8(1):51-65.
Verbrugge et al., "Revisiting diastolic filling time as mechanistic insight for response to cardiac resynchronization therapy," *Europace*, Dec. 2013; 15(12):1747-56.
Verrier et al., "Mechanisms of ranolazine's dual protection against atrial and ventricular fibrillation," *Europace*, Mar. 2013; 15(3):317-324.
Verrijcken et al., "Pacemaker-mediated tachycardia with varying cycle length: what is the mechanism?" *Europace*, Oct. 2009; 11(10):1400-2.
Villani et al., "Reproducibility of internal atrial defibrillation threshold in paroxysmal and persistent atrial fibrillation," *Europace*, Jul. 2004; 6(4):267-72.
Violi et al., "Antioxidants for prevention of atrial fibrillation: a potentially useful future therapeutic approach? A review of the literature and meta-analysis," *Europace*, Aug. 2014; 16(8):1107-1116.
Weber et al., "Adenosine sensitive focal atrial tachycardia originating from the non-coronary aortic cusp," *Europace*, Jun. 2009; 11(6):823-6.
Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intra-atrial conduction delay," *Europace*, Dec. 2011; 13(12):1681-7.
Weiss et al., "The influence of fibre orientation, extracted from different segments of the human left ventricle, on the activation and repolarization sequence: a simulation study," *Europace*, Nov. 2007; 9(Suppl. 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.
Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion," *Pacing Clin Electrophysiol.*, Aug. 2008; 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.
Yang et al., "Focal atrial tachycardia originating from the distal portion of the left atrial appendage: Characteristics and long-term outcomes of radiofrequency ablation," *Europace*, Feb. 2012; 14(2):254-60.
Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording monophasic action potentials using a platinum-electrode ablation catheter," *Europace*, Oct. 2000; 2(4):312-9.
Yusuf et al., "5-Hydroxytryptamine and Atrial Fibrillation: How Significant is This Piece in the Puzzle?" *J Cardiovasc Electrophysiol.*, Feb. 2003; 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acute atrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short- and long-term cardiac memory," *Europace*, Sep. 2004; 6(5):418-24.
Zografos et al., "Inhibition of the renin-angiotensin system for prevention of atrial fibrillation," *Pacing Clin Electrophysiol.*, Oct. 2010; 33(10):1270-85.
(PCT/US2014/066792) PCT Notification of Transmittal of the International Search Report and the Written Opinion of the International Searching Authority.
(PCT/US2014/013601) PCT Notification of Transmittal of the International Search Report and the Written Opinion of the International Searching Authority.
(PCT/US2014/036782) PCT Notification of Transmittal of the International Search Report and the Written Opinion of the International Searching Authority, dated Aug. 22, 2014, 11 pages.
International Search Report and Written Opinion for Application No. PCT/US2017/047378, 8 pages, dated Dec. 6, 2017.
(PCT/US2018/050988) PCT Notification of Transmittal of the International Search Report and the Written Opinion of the International Searching Authority, dated Nov. 14, 2018, 11 pages.
(PCT/US2018/050993) PCT Notification of Transmittal of the International Search Report and the Written Opinion of the International Searching Authority, dated Nov. 16, 2018, 7 pages.
(PCT/US2019/023642) PCT Notification of Transmittal of the International Search Report and the Written Opinion of the International Searching Authority, dated Jun. 28, 2019, 14 pages.

\* cited by examiner

CARDIAC CONDUCTION SYSTEM CAPTURE

The disclosure herein relates to systems, methods, and devices for use in determining cardiac conduction system capture of, for example, ventricle from atrium (VfA) cardiac therapy.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

When implanting a pacing electrode and during delivery of pacing therapy using such pacing electrode, it can be challenging to determine whether the pacing electrode and pacing therapy delivered thereby have captured the cardiac conduction system or other cardiac tissue.

SUMMARY

The illustrative systems, devices, and methods described herein may be configured to assist a user (e.g., a physician) determining whether a pacing electrode such as ventricle from atrium (VfA) pacing electrode, and the cardiac therapy delivered thereby, has captured the cardiac conduction system as opposed to other cardiac tissue during one or both of implantation and after implantation. Further, the illustrative systems, devices, and methods described herein may be configured to assist a user (e.g., a physician) determining whether the patient has A-V block (e.g., no natural conduction from the atria to ventricles across the A-V node).

In one or more embodiments, the systems, devices, and methods may be described as being noninvasive. For example, in some embodiments, the systems, devices, and methods may not need, or include, implantable devices such as leads, probes, sensors, catheters, implantable electrodes, etc. to monitor, or acquire, a plurality of cardiac signals from tissue of the patient for use in determining capture of the cardiac conduction system (as opposed to capture of other cardiac tissue) and A-V block. Instead, the systems, devices, and methods may use electrical measurements taken noninvasively using, e.g., a plurality of external electrodes attached to the skin of a patient about the patient's torso. In one or more embodiments, the systems, devices, and methods may be described as being invasive in that such systems, devices, and methods may utilize implantable electrodes to monitor electrical activity for using in determining, or evaluating, cardiac conduction system capture and/or A-V block. Additionally, it is be understood that both invasive and non-invasive apparatus and processes may be used at the same time or simultaneously in some embodiments.

It may be described that the illustrative systems, devices, and methods relate to ventricle from atrium (VfA) pacing as will be further described herein. The VfA pacing may result in capture of myocardium alone without capturing the cardiac conduction system. Determination of capture of the cardiac conduction system may be described as being useful for determining, or evaluating, placement of the lead and/or pacing device delivering VfA pacing therapy. In one embodiment, the illustrative systems, devices, and methods may be generally described as including delivering pacing at an A-V delay, or interval, equal to 70% of patient's intrinsic A-V delay and progressively decreasing the A-V delay, or interval, in steps of about 10 milliseconds (ms) to about 20 ms until a predefined minimum of 60 ms. Electrical activity from one or more of an external electrode apparatus and interval electrode apparatus (e.g., activation times, electrograms, and electrocardiograms) may be measured, and dyssynchrony information may be determined, or generated, based on the measured electrical activity.

In the absence of cardiac conduction system capture, dyssynchrony at shorter A-V pacing intervals may increase to due to cell-to-cell conduction. In one or more embodiments, capture of the cardiac conduction system may be determined if an electrical dyssynchrony value (e.g., generated from electrical activity monitored from electrode apparatus) is low at an initial A-V delay, or interval, pacing (e.g., standard deviation of activation times (SDAT) is less than or equal to about 25 ms, average left ventricular or thoracic surrogate electrical activation times (LVAT) is less than or equal to about 40 ms, etc.) and the electrical dyssynchrony value continues to stay low at shorter A-V pacing intervals. In one or more embodiments, capture of the cardiac conduction system may be determined if electrocardiograms (ECG) and/or electrograms (EGM) at short A-V pacing intervals are similar (e.g., closely match, within a tolerance level, etc.) to the ECGs and/or EGMs at longer AV pacing intervals in terms of one or both of QRS morphology and duration.

One illustrative system may include electrode apparatus comprising a plurality of electrodes to monitor electrical activity from tissue of a patient and computing apparatus comprising processing circuitry and coupled to the electrode apparatus. The computing apparatus may be configured to monitor electrical activity of the patient's heart using one or more electrodes of the plurality of electrodes during delivery of ventricle from atrium (VfA) pacing therapy at a plurality of diagnostic A-V delays, wherein each of the plurality of diagnostic A-V delays are less than the patient's intrinsic A-V delay, and determine whether the VfA pacing therapy has captured the cardiac conduction system based on the monitored electrical activity during delivery of VfA pacing therapy at the plurality of diagnostic A-V delays.

One illustrative method may include monitoring electrical activity of the patient's heart using one or more electrodes of a plurality of electrodes during delivery of ventricle from atrium (VfA) pacing therapy at a plurality of diagnostic A-V delays, wherein each of the plurality of diagnostic A-V delays are less than the patient's intrinsic A-V delay, and determining whether the VfA pacing therapy has captured the cardiac conduction system based on the monitored electrical activity during delivery of VfA pacing therapy at the plurality of diagnostic A-V delays.

One illustrative implantable medical device may include a plurality of electrodes comprising a right atrial electrode positionable within the right atrium to deliver cardiac therapy to, or sense electrical activity of, the right atrium of a patient's heart, and a tissue-piercing electrode implantable through the right atrial endocardium and central fibrous body to deliver cardiac therapy to, or sense electrical activity of, the left ventricle of a patient's heart. The illustrative device may further include a therapy delivery circuit operably coupled to the plurality of electrodes to deliver cardiac therapy to the patient's heart and a sensing circuit operably coupled to the plurality of electrodes to sense electrical activity of the patient's heart. The illustrative device may further include a controller comprising processing circuitry operably coupled to the therapy delivery circuit and the sensing circuit. The controller may be configured to deliver ventricle from atrium (VfA) pacing therapy using at least the tissue-piercing electrode at a plurality of diagnostic A-V delays, wherein each of the plurality of diagnostic A-V delays are less than the patient's intrinsic A-V delay, monitor electrical activity of the patient's heart using one or more electrodes of the plurality of electrodes during delivery of VfA pacing therapy at the plurality of diagnostic A-V delays, and determine whether the VfA pacing therapy has captured the cardiac conduction system based on the monitored electrical activity during delivery of VfA pacing therapy at the plurality of diagnostic A-V delays.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF ILLUSTRATIVE EMBODIMENTS

Figure 1:
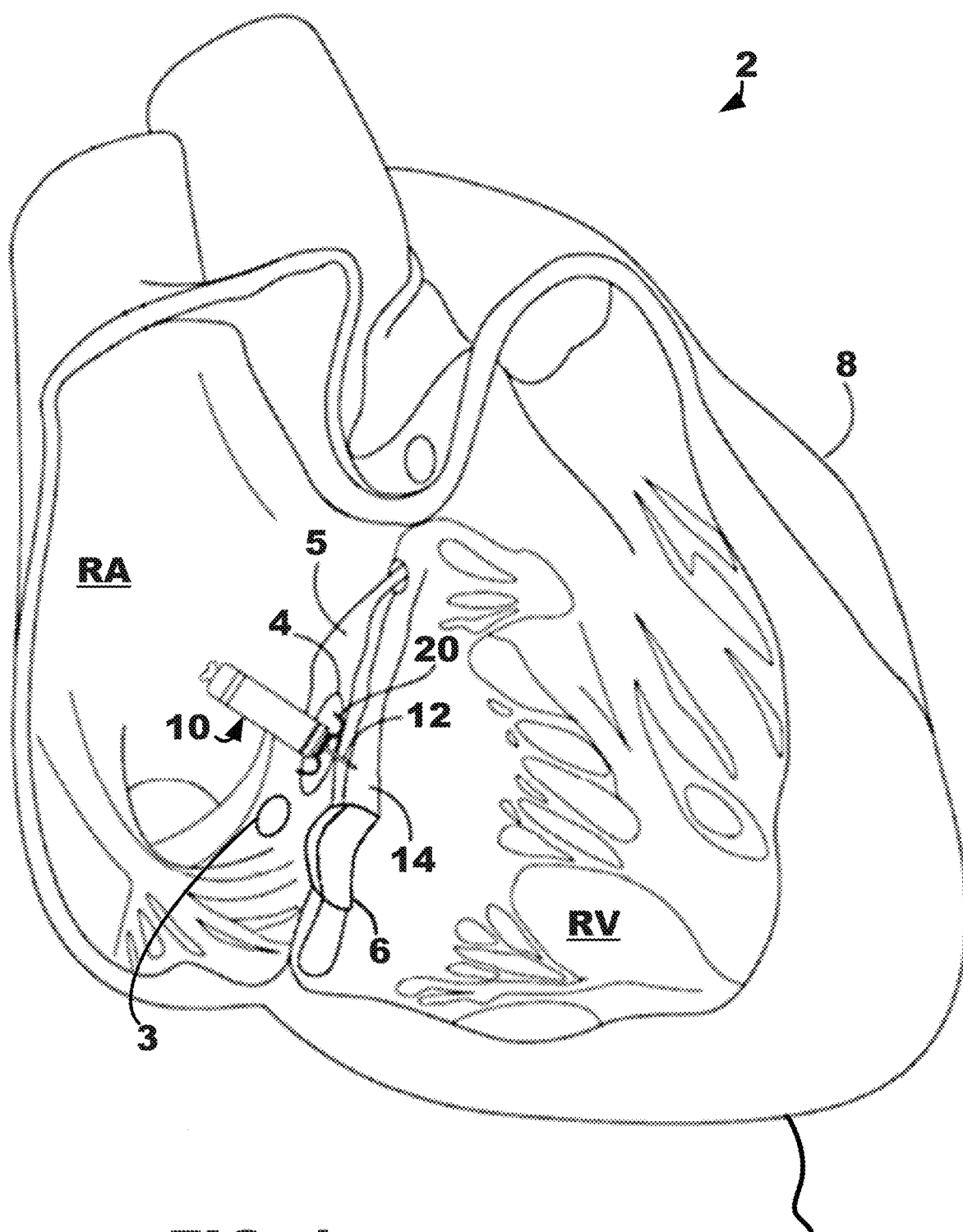
FIG. 1 is a conceptual diagram of an illustrative cardiac therapy system including an intracardiac medical device implanted in a patient's heart and a separate medical device positioned outside of the patient's heart.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative systems, methods, and devices shall be described with reference to FIGS. 1-11. It will be apparent to one skilled in the art that elements or processes from one embodiment may be used in combination with elements or processes of the other embodiments, and that the possible embodiments of such systems, methods, and devices using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 depicts an illustrative ventricle from atrium (VfA) cardiac therapy system that may be configured to be used with, for example, the systems and methods described herein with respect to FIGS. 1-11. Although it is to be understood that the present disclosure may utilize one or both of leadless and leaded implantable medical devices, the illustrative cardiac therapy system of FIG. 1 includes a leadless intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device 10 against the atrial endocardium in a target implant region 4. The target implant region 4 may lie between the Bundle of His 5 and the coronary sinus 3 and may be adjacent, or next to, the tricuspid valve 6. The device 10 may be described as a ventricle-from-atrium device because, for example, the device 10 may perform, or execute, one or both of sensing electrical activity from and providing therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. Further, although a leadless device may have a lead, the lead would not extend from outside of the patient's heart to inside of the patient's heart or would not extend from inside of the patient's heart to outside of the patient's heart. Some leadless devices may be introduced through a vein, but once implanted, the device is free of, or may not include, any transvenous lead and may be configured to provide cardiac therapy without using any transvenous lead. Further, a leadless VfA device, in particular, does not use a lead to operably connect to an electrode in the ventricle when a housing of the device is positioned in the atrium. Additionally, a leadless electrode may be coupled to the housing of the medical device without using a lead between the electrode and the housing.

The device 10 may include a dart electrode assembly 12 defining, or having, a straight shaft extending from a distal end region of device 10. The dart electrode assembly 12 may be placed, or at least configured to be placed, through the atrial myocardium and the central fibrous body and into the ventricular myocardium 14, or along the ventricular septum, without perforating entirely through the ventricular endocardial or epicardial surfaces. The dart electrode assembly 12 may carry, or include, an electrode at a distal end region of the shaft such that the electrode may be positioned within the ventricular myocardium for sensing ventricular signals and delivering ventricular pacing pulses (e.g., to depolarize the left ventricle and/or right ventricle to initiate a contraction of the left ventricle and/or right ventricle). In some examples, the electrode at the distal end region of the shaft is a cathode electrode provided for use in a bipolar electrode pair for pacing and sensing. While the implant region 4 as illustrated may enable one or more electrodes of the dart electrode assembly 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

It is to be understood that although device 10 is described herein as including a single dart electrode assembly, the device 10 may include more than one dart electrode assembly placed, or configured to be placed, through the atrial myocardium and the central fibrous body, and into the ventricular myocardium 14, or along the ventricular septum, without perforating entirely through the ventricular endocardial or epicardial surfaces. Additionally, each dart electrode assembly may carry, or include, more than a single electrode at the distal end region, or along other regions (e.g., proximal or central regions), of the shaft.

The cardiac therapy system 2 may also include a separate medical device 50 (depicted diagrammatically in FIG. 1), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead including, or carrying, a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy (e.g., defibrillation shocks provided by the defibrillation electrode of the defibrillation lead), the separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may further include a sensing circuit. The sensing circuit may be configured to obtain electrical signals sensed via one or more combinations of electrodes and to process the obtained signals. The components of the sensing circuit may include analog components, digital components, or a combination thereof. The sensing circuit may, for example, include one or more sense amplifiers, filters, rectifiers, threshold detectors, analog-to-digital converters (ADCs), or the like. The sensing circuit may convert the sensed signals to digital form and provide the digital signals to the control circuit for processing and/or analysis. For example, the sensing circuit may amplify signals from sensing electrodes and convert the amplified signals to multi-bit digital signals by an ADC, and then provide the digital signals to the control circuit. In one or more embodiments, the sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical-pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 2:
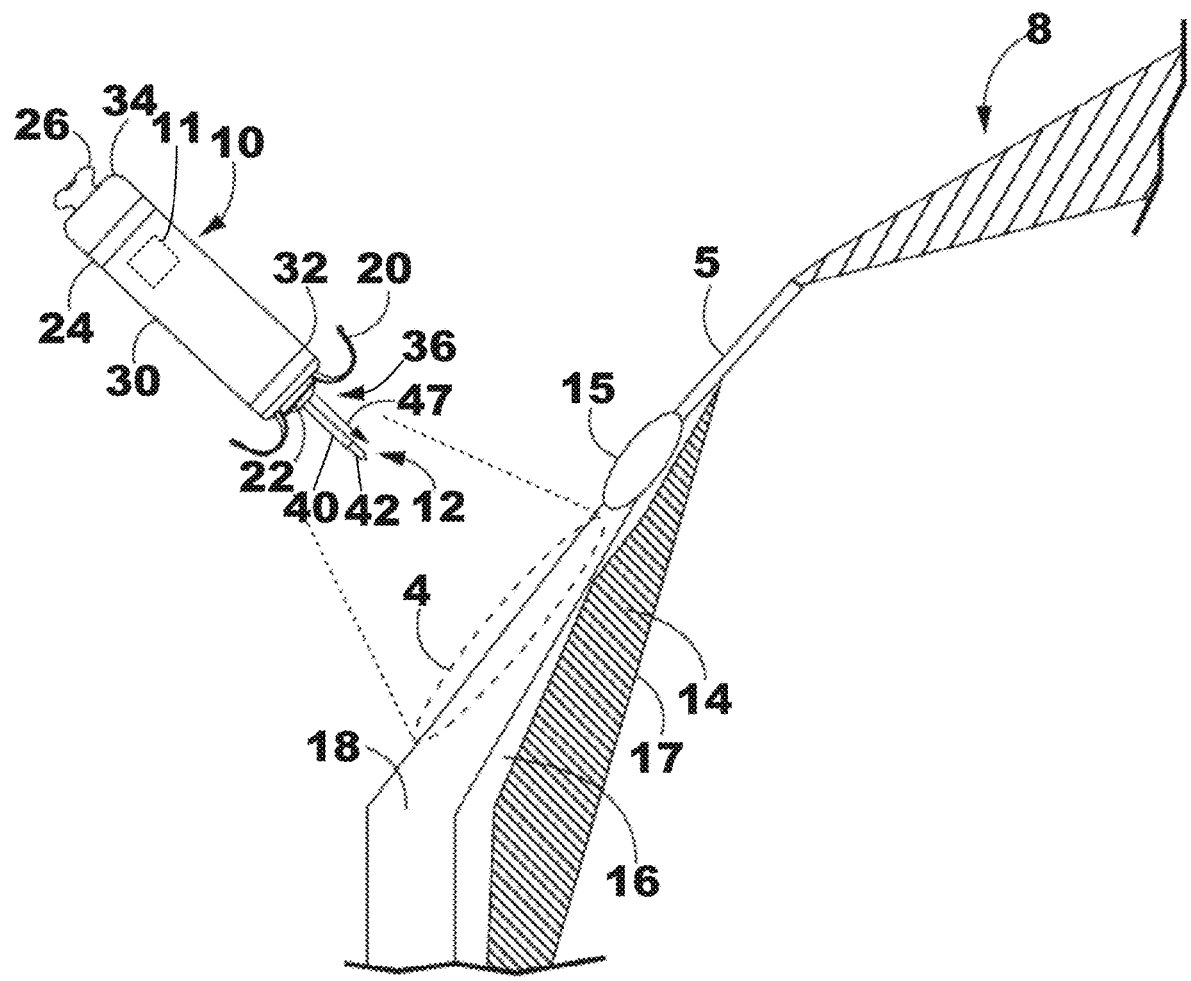
FIG. 2 is an enlarged conceptual diagram of the intracardiac medical device of FIG. 1 and anatomical structures of the patient's heart.

FIG. 2 is an enlarged conceptual diagram of the intracardiac medical device 10 of FIG. 1 and anatomical structures of the patient's heart 8. In particular, the device 10 is configured to sense cardiac signals and/or deliver pacing therapy. The intracardiac device 10 may include a housing 30. The housing 30 may define a hermetically-sealed internal cavity in which internal components of the device 10 reside, such as a sensing circuit, therapy delivery circuit, control circuit, memory, telemetry circuit, other optional sensors, and a power source as generally described in conjunction with FIG. 6. The housing 30 may include (e.g., be formed of or from) an electrically conductive material such as, e.g., titanium or titanium alloy, stainless steel, MP35N (a non-magnetic nickel-cobalt-chromium-molybdenum alloy), platinum alloy, or other bio-compatible metal or metal alloy. In other examples, the housing 30 may include (e.g., be formed of or from) a non-conductive material including ceramic, glass, sapphire, silicone, polyurethane, epoxy, acetyl co-polymer plastics, polyether ether ketone (PEEK), a liquid crystal polymer, or other biocompatible polymer.

In at least one embodiment, the housing 30 may be described as extending between a distal end region 32 and a proximal end region 34 and as defining a generally-cylindrical shape, e.g., to facilitate catheter delivery. In other embodiments, the housing 30 may be prismatic or any other shape to perform the functionality and utility described herein. The housing 30 may include a delivery tool interface member 26, e.g., defined, or positioned, at the proximal end region 34, for engaging with a delivery tool during implantation of the device 10.

All or a portion of the housing 30 may function as a sensing and/or pacing electrode during cardiac therapy. In the example shown, the housing 30 includes a proximal housing-based electrode 24 that circumscribes a proximal portion (e.g., closer to the proximal end region 34 than the distal end region 32) of the housing 30. When the housing 30 is (e.g., defines, formed from, etc.) an electrically-conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to form, or define, the proximal housing-based electrode 24. When the housing 30 is (e.g., defines, formed from, etc.) a non-conductive material, such as a ceramic, glass or polymer material, an electrically-conductive coating or layer, such as a titanium, platinum, stainless steel, or alloys thereof, may be applied to one or more discrete areas of the housing 30 to form, or define, the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32, and therefore, may be referred to as a proximal housing-based electrode 24. In other examples, however, the proximal housing-based electrode 24 may be located at other positions along the housing 30, e.g., more distal relative to the position shown.

At the distal end region 32, the device 10 may include a distal fixation and electrode assembly 36, which may include one or more fixation members 20 and one or more dart electrode assemblies 12 of equal or unequal length. In one such example as shown, a single dart electrode assembly 12 includes a shaft 40 extending distally away from the housing distal end region 32 and one or more electrode elements, such as a tip electrode 42 at or near the free, distal end region of the shaft 40. The tip electrode 42 may have a conical or hemi-spherical distal tip with a relatively narrow tip-diameter (e.g., less than about 1 millimeter (mm)) for penetrating into and through tissue layers without using a sharpened tip or needle-like tip having sharpened or beveled edges.

The dart electrode assembly 12 may be configured to pierce through one or more tissue layers to position the tip electrode 42 within a desired tissue layer such as, e.g., the ventricular myocardium. As such, the height 47, or length, of the shaft 40 may correspond to the expected pacing site depth, and the shaft 40 may have a relatively-high compressive strength along its longitudinal axis to resist bending in a lateral or radial direction when pressed against and into the implant region 4. If a second dart electrode assembly 12 is employed, its length may be unequal to the expected pacing site depth and may be configured to act as an indifferent electrode for delivering of pacing energy to and/or sensing signals from the tissue. In one embodiment, a longitudinal axial force may be applied against the tip electrode 42, e.g., by applying longitudinal pushing force to the proximal end 34 of the housing 30, to advance the dart electrode assembly 12 into the tissue within the target implant region.

The shaft 40 may be described as longitudinally non-compressive and/or elastically deformable in lateral or radial directions when subjected to lateral or radial forces to allow temporary flexing, e.g., with tissue motion, but may return to its normally straight position when lateral forces diminish. Thus, the dart electrode assembly 12 including the shaft 40 may be described as being resilient. When the shaft 40 is not exposed to any external force, or to only a force along its longitudinal central axis, the shaft 40 may retain a straight, linear position as shown.

In other words, the shaft 40 of the dart electrode assembly 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by a height, or length, 47 of the shaft 40.

The one or more fixation members 20 may be described as one or more "tines" having a normally curved position. The tines may be held in a distally extended position within a delivery tool. The distal tips of tines may penetrate the heart tissue to a limited depth before elastically, or resiliently, curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode assembly 12 may at least partially define the height 47, or length, of the shaft 40 for penetrating through the atrial endocardium 18 in the target implant region 4, through the central fibrous body 16, and into the ventricular myocardium 14 without perforating through the ventricular endocardial surface 17. When the height 47, or length, of the dart electrode assembly 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode assembly 12 may have a total combined height 47, or length, of tip electrode 42 and shaft 40 from about 3 mm to about 8 mm in various examples. The diameter of the shaft 40 may be less than about 2 mm, and may be about 1 mm or less, or even about 0.6 mm or less.

The device 10 may include an acoustic and/or motion detector 11 within the housing 30. The acoustic or motion detector 11 may be operably coupled to one or more of a control circuit 80, a sensing circuit 86, or a therapy delivery circuit 84 as described with respect to FIG. 6. The acoustic and/or motion detector 11 may be used to monitor mechanical activity, such as atrial mechanical activity (e.g., an atrial contraction) and/or ventricular mechanical activity (e.g., a ventricular contraction). In some embodiments, the acoustic and/or motion detector 11 may be used to detect right atrial mechanical activity. A non-limiting example of an acoustic and/or motion detector 11 includes one or both of an accelerometer and a microphone. In some embodiments, the mechanical activity detected by the acoustic and/or motion detector 11 may be used to supplement or replace electrical activity detected by one or more of the electrodes of the device 10. For example, the acoustic and/or motion detector 11 may be used in addition to, or as an alternative to, the proximal housing-based electrode 24.

The acoustic and/or motion detector 11 may also be used for rate response detection or to provide a rate-responsive IMD. Various techniques related to rate response may be described in U.S. Pat. No. 5,154,170 (Bennett et al.), issued Oct. 13, 1992, entitled "Optimization for rate responsive cardiac pacemaker," and U.S. Pat. No. 5,562,711 (Yerich et al.), issued Oct. 8, 1996, entitled "Method and apparatus for rate-responsive cardiac pacing," each of which is incorporated herein by reference in its entirety.

In various embodiments, acoustic and/or motion sensor 11 may be used as a heart sound (HS) sensor and may be implemented as a microphone and/or a 1-, 2- or 3-axis accelerometer. In one embodiment, the acoustic and/or motion sensor 11 is implemented as a piezoelectric crystal mounted within the housing 30 that is responsive to the mechanical motion associated with heart sounds. Examples of other embodiments of acoustical sensors that may be adapted for implementation with the techniques of the present disclosure may be described generally in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), each of which is incorporated herein by reference in its entirety.

In other words, various types of acoustic and/or motion sensors 11 may be used. For example, the acoustic and/or motion sensor 11 may be described as being any implantable or external sensor responsive to one or more of the heart sounds, and thereby, capable of producing, or generating, an electrical analog signal correlated in time and amplitude to the heart sounds. The analog signal may be then be processed, which may include digital conversion, by a HS sensing module to obtain HS parameters, such as amplitudes or relative time intervals, as derived by the HS sensing module or control circuit 80. The acoustic and/or motion sensor 11 and the HS sensing module may be incorporated in an IMD such as, e.g., device 10, capable of delivering CRT or another cardiac therapy being optimized or may be implemented in a separate device having wired or wireless communication with another IMD or an external programmer or computer used during a pace parameter optimization procedure as described herein.

Figure 3:
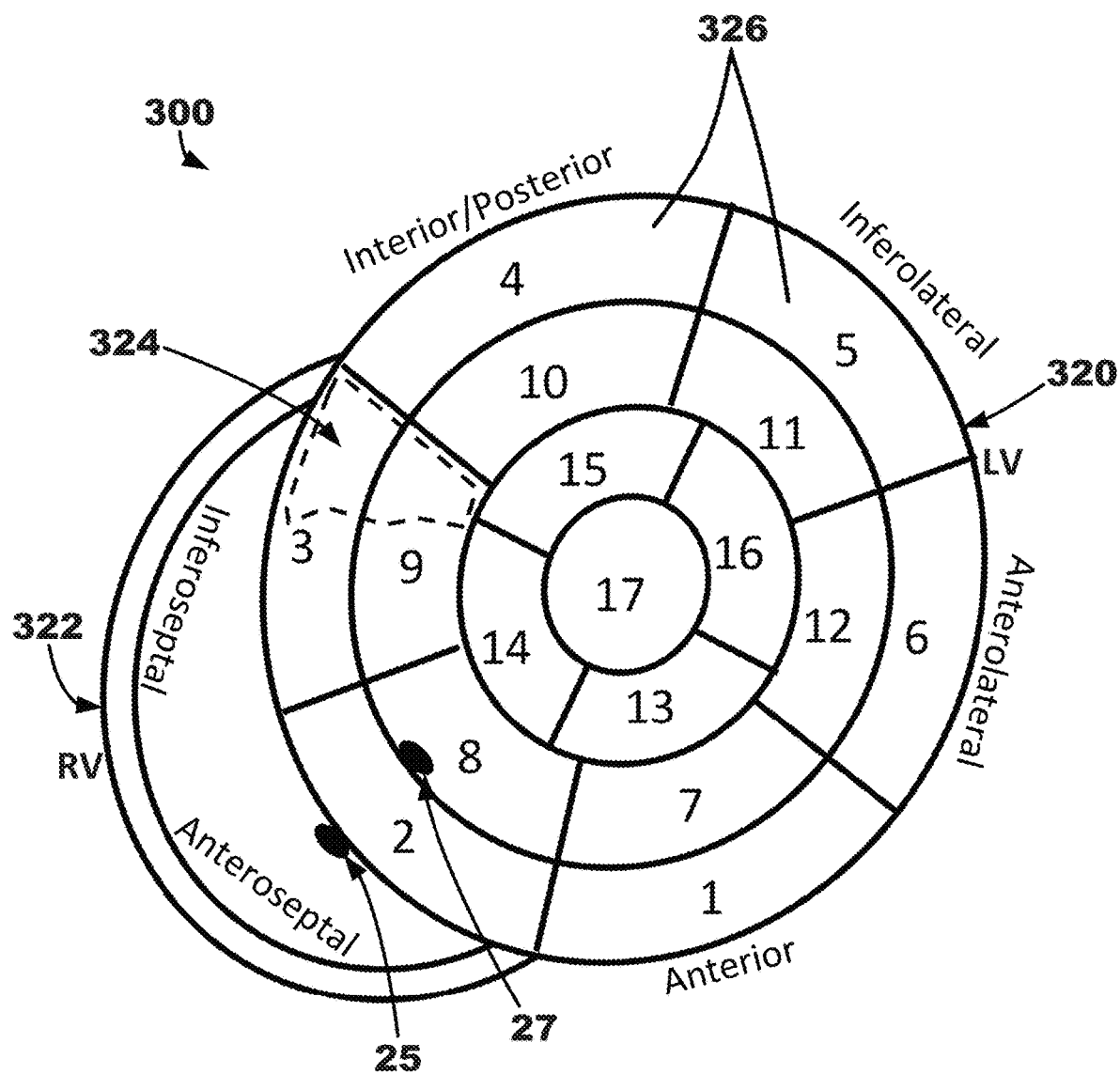
FIG. 3 is a conceptual diagram of a map of a patient's heart in a standard 17 segment view of the left ventricle showing various electrode implantation locations for use with the illustrative systems and devices described herein.

FIG. 3 is a two-dimensional (2D) ventricular map 300 of a patient's heart (e.g., a top-down view) showing the left ventricle 320 in a standard 17 segment view and the right ventricle 322. The map 300 defines, or includes, a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) 25 and left bundle branch (LBB) 27.

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body. Once implanted, the tissue-piercing electrode may be positioned in the target implant region 4 (FIGS. 1-2), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of one or more of the basal inferoseptal area 3 and mid-inferoseptal area 9 (e.g., the basal inferoseptal area only, the mid-inferoseptal area only, or both the basal inferoseptal area and the mid-inferoseptal area). For example, the high inferior/posterior basal septal region may include region 324 illustrated generally as a dashed-line boundary. As shown, the dashed line boundary represents an approximation of where the high inferior/posterior basal septal region is located, which may take a somewhat different shape or size depending on the particular application.

Figure 4:
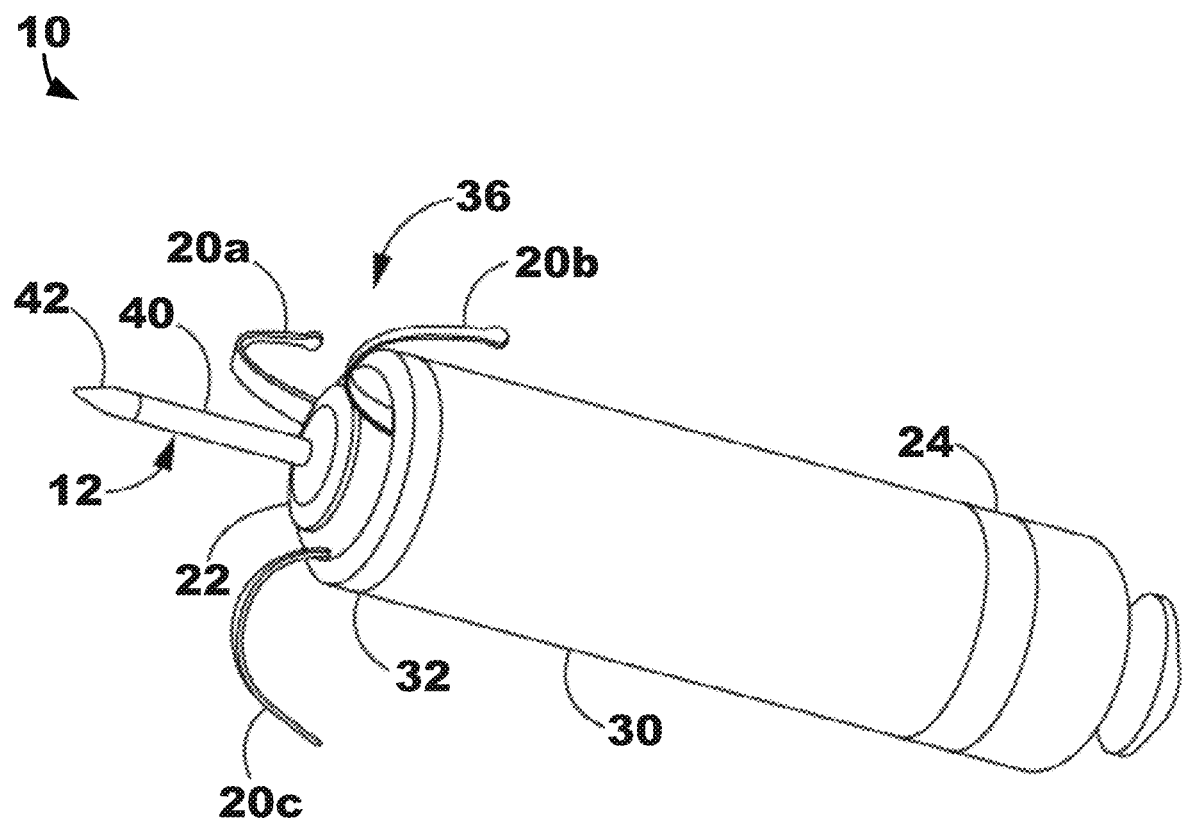
FIG. 4 is a perspective view of an illustrative intracardiac medical device having a distal fixation and electrode assembly that includes a distal housing-based electrode implemented as a ring electrode for use with the illustrative systems and devices described herein.

FIG. 4 is a three-dimensional perspective view of the device 10 capable of delivering pacing therapy and sensing cardiac signals. As shown, the distal fixation and electrode assembly 36 includes the distal housing-based electrode 22 implemented as a ring electrode. The distal housing-based electrode 22 may be positioned in intimate contact with or operative proximity to atrial tissue when fixation member tines 20a, 20b and 20c of the fixation members 20, engage with the atrial tissue. The tines 20a, 20b and 20c, which may be elastically deformable, may be extended distally during delivery of device 10 to the implant site. For example, the tines 20a, 20b, and 20c may pierce the atrial endocardial surface as the device 10 is advanced out of the delivery tool and flex back into their normally curved position (as shown) when no longer constrained within the delivery tool. As the tines 20a, 20b and 20c curve back into their normal position, the fixation member 20 may "pull" the distal fixation member and electrode assembly 36 toward the atrial endocardial surface. As the distal fixation member and electrode assembly 36 is "pulled" toward the atrial endocardium, the tip electrode 42 may be advanced through the atrial myocardium and the central fibrous body and into the ventricular myocardium. The distal housing-based electrode 22 may then be positioned against, or adjacent, the atrial endocardial surface.

The distal housing-based electrode 22 may include (e.g., be formed of) an electrically conductive material, such as, e.g., titanium, platinum, iridium, or alloys thereof. In one embodiment, the distal housing-based electrode 22 may be a single, continuous ring electrode. In other examples, portions of the distal housing-based electrode 22 may be coated with an electrically insulating coating such as, e.g., parylene, polyurethane, silicone, epoxy, or other insulating coating, to reduce the electrically conductive surface area of the electrode. For instance, one or more sectors of the distal housing-based electrode 22 may be coated to separate two or more electrically conductive exposed surface areas of the distal housing-based electrode 22. Reducing the electrically conductive surface area of the distal housing-based electrode 22, e.g., by covering portions of the electrically conductive areas with an insulating coating, may increase the electrical impedance of the distal housing-based 22, and thereby, reduce the current delivered during a pacing pulse that captures the myocardium, e.g., the atrial myocardial tissue. A lower current drain may conserve the power source, e.g., one or more rechargeable or non-rechargeable batteries, of the device 10.

As described above, the distal housing-based electrode 22 may be configured as an atrial cathode electrode for delivering pacing pulses to the atrial tissue at the implant site 4 in combination with the proximal housing-based electrode 24 as the return anode. The electrodes 22 and 24 may be used to sense atrial P-waves for use in controlling atrial pacing pulses (delivered in the absence of a sensed P-wave) and for controlling atrial-synchronized ventricular pacing pulses delivered using the tip electrode 42 as a cathode and the proximal housing-based electrode 24 as the return anode. In other examples, the distal housing-based electrode 22 may be used as a return anode in conjunction with the cathode tip electrode 42 for ventricular pacing and sensing.

Figure 5:
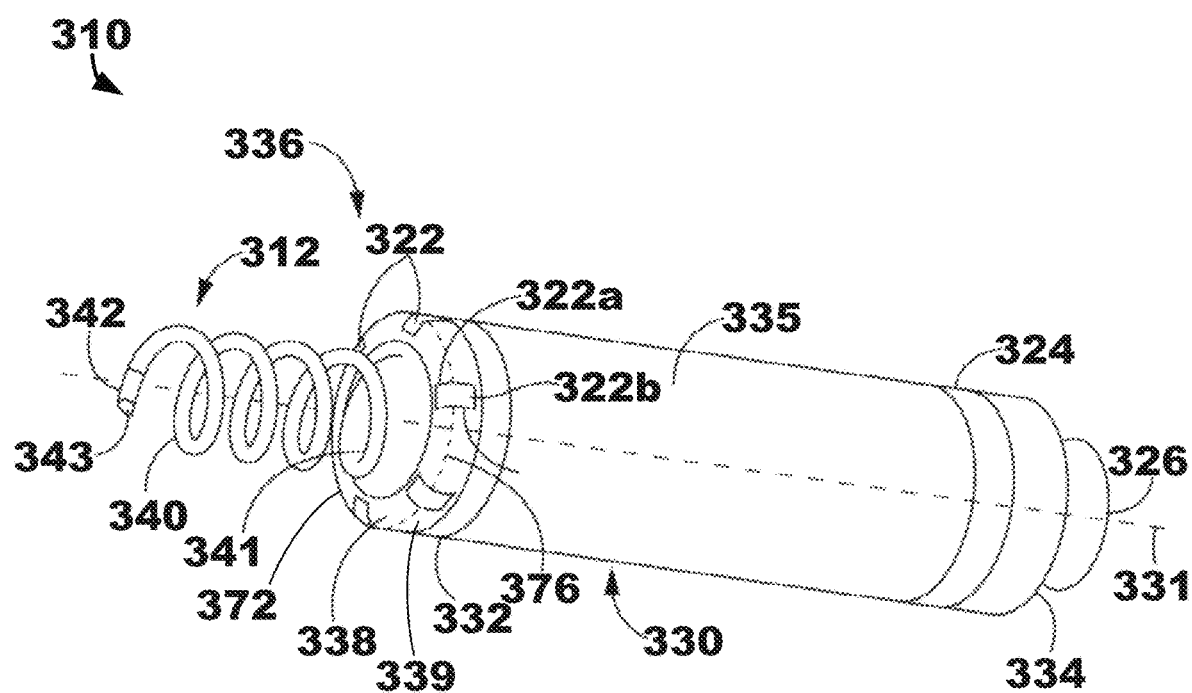
FIG. 5 is a perspective view of another illustrative intracardiac medical device for use with the illustrative systems and devices described herein.

FIG. 5 is a three-dimensional perspective view of another leadless intracardiac medical device 310 that may be configured for determining cardiac conduction system capture, calibrating pacing therapy, and/or delivering pacing therapy for single or multiple chamber cardiac therapy (e.g., dual or triple chamber cardiac therapy) according to another example. The device 310 may include a housing 330 having an outer sidewall 335, shown as a cylindrical outer sidewall, extending from a housing distal end region 332 to a housing proximal end region 334. The housing 330 may enclose electronic circuitry configured to perform single or multiple chamber cardiac therapy, including atrial and ventricular cardiac electrical signal sensing and pacing the atrial and ventricular chambers. Delivery tool interface member 326 is shown on the housing proximal end region 334.

A distal fixation and electrode assembly 336 may be coupled to the housing distal end region 332. The distal fixation and electrode assembly 336 may include an electrically insulative distal member 372 coupled to the housing distal end region 332. The tissue-piercing electrode assembly 312 may extend away from the housing distal end region 332, and multiple non-tissue piercing electrodes 722 may be coupled directly to the insulative distal member 372. The tissue-piercing electrode assembly 312, as shown, extends in a longitudinal direction away from the housing distal end region 332 and may be coaxial with the longitudinal center axis 331 of the housing 330.

The distal tissue-piercing electrode assembly 312 may include an electrically insulated shaft 340 and a tip electrode 342 (e.g., tissue-piercing electrode). In some examples, the tissue-piercing electrode assembly 312 may be described as an active fixation member including a helical shaft 340 and a distal cathode tip electrode 342. The helical shaft 340 may extend from a shaft distal end region 343 to a shaft proximal end region 341, which may be directly coupled to the insulative distal member 372. The helical shaft 340 may be coated with an electrically insulating material, e.g., parylene or other examples listed herein, to avoid sensing or stimulation of cardiac tissue along the shaft length.

The tip electrode 342 is located, or positioned, at the shaft distal end region 343 and may serve as a cathode electrode for delivering ventricular pacing pulses and sensing ventricular electrical signals using the proximal housing-based electrode 324 as a return anode when the tip electrode 342 is advanced proximate or into ventricular tissue as described herein. The proximal housing-based electrode 324 may be a ring electrode circumscribing the housing 330 and may be defined by an uninsulated portion of the longitudinal sidewall 335. Other portions of the housing 330 not serving as an electrode may be coated with an electrically insulating material similar to as described above in conjunction with the device 10 of FIG. 4.

Using two or more tissue-piercing electrodes (e.g., of any type) penetrating into the LV myocardium may be used for more localized pacing capture and may mitigate ventricular pacing spikes affecting capturing atrial tissue. In some embodiments, multiple tissue-piercing electrodes may include two or more dart-type electrode assemblies (e.g., electrode assembly 12 of FIG. 4), a helical-type electrode. Non-limiting examples of multiple tissue-piercing electrodes include two dart electrode assemblies, a helix electrode with a dart electrode assembly extending therethrough (e.g., through the center), or dual intertwined helixes. Multiple tissue-piercing electrodes may also be used for bipolar or multi-polar pacing.

In some embodiments, one or more tissue-piercing electrodes (e.g., of any type) that penetrate into the LV myocardium may be a multi-polar tissue-piercing electrode. A multi-polar tissue-piercing electrode may include one or more electrically-active and electrically-separate elements, which may enable bipolar or multi-polar pacing from one or more tissue-piercing electrodes. In other words, each tissue piercing electrode may include one or more separate electrodes or electrically active segments, or areas, that are independent from one another.

Multiple non-tissue piercing electrodes 322 may be provided along a periphery of the insulative distal member 372, peripheral to the tissue-piercing electrode assembly 312. The insulative distal member 372 may define a distal-facing surface 338 of the device 310 and a circumferential surface 339 that circumscribes the device 310 adjacent to the housing longitudinal sidewall 335. Non-tissue piercing electrodes 322 may be formed of an electrically conductive material, such as titanium, platinum, iridium, or alloys thereof. In the illustrated embodiment, six non-tissue piercing electrodes 322 are spaced apart radially at equal distances along the outer periphery of insulative distal member 372, however, two or more non-tissue piercing electrodes 322 may be provided.

Non-tissue piercing electrodes 322 may be discrete components each retained within a respective recess 374 in the insulative member 372 sized and shaped to mate with the non-tissue piercing electrode 322. In other examples, the non-tissue piercing electrodes 322 may each be an uninsulated, exposed portion of a unitary member mounted within or on the insulative distal member 372. Intervening portions of the unitary member not functioning as an electrode may be insulated by the insulative distal member 372 or, if exposed to the surrounding environment, may be coated with an electrically insulating coating, e.g., parylene, polyurethane, silicone, epoxy, or other insulating coating.

When the tissue-piercing electrode assembly 312 is advanced into cardiac tissue, at least one non-tissue piercing electrode 322 may be positioned against, in intimate contact with, or in operative proximity to, a cardiac tissue surface for delivering pulses and/or sensing cardiac electrical signals produced by the patient's heart. For example, non-tissue piercing electrodes 322 may be positioned in contact with right atrial endocardial tissue for pacing and sensing in the atrium when the tissue-piercing electrode assembly 312 is advanced into the atrial tissue and through the central fibrous body until the distal tip electrode 342 is positioned in direct contact with ventricular tissue, e.g., ventricular myocardium and/or a portion of the ventricular conduction system.

Non-tissue piercing electrodes 322 may be coupled to therapy delivery circuit and sensing circuit as will be described herein with respect to FIG. 6 enclosed by the housing 330 to function collectively as a cathode electrode for delivering atrial pacing pulses and for sensing atrial electrical signals, e.g., P-waves, in combination with the proximal housing-based electrode 324 as a return anode. Switching circuitry included in a sensing circuit may be activated under the control of a control circuit to couple one or more of the non-tissue piercing electrodes to an atrial sensing channel. Distal, non-tissue piercing electrodes 322 may be electrically isolated from each other so that each individual one of the electrodes 322 may be individually selected by switching circuitry included in a therapy delivery circuit to serve alone or in a combination of two or more of the electrodes 322 as an atrial cathode electrode. Switching circuitry included in a therapy delivery circuit may be activated under the control of a control circuit to couple one or more of the non-tissue piercing electrodes 322 to an atrial pacing circuit. Two or more of the non-tissue piercing electrodes may be selected at a time to operate as a multi-point atrial cathode electrode.

Certain non-tissue piercing electrodes 322 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 322 functioning as a cathode electrode that provides an optimal combination of a low pacing capture threshold amplitude and relatively high electrode impedance may be selected to achieve reliable atrial pacing using minimal current drain from a power source.

In some instances, the distal-facing surface 338 may uniformly contact the atrial endocardial surface when the tissue-piercing electrode assembly 312 anchors the housing 330 at the implant site 4. In that case, all the electrodes 322 may be selected together to form the atrial cathode. Alternatively, every other one of the electrodes 322 may be selected together to form a multi-point atrial cathode having a higher electrical impedance that is still uniformly distributed along the distal-facing surface 338. Alternatively, a subset of one or more electrodes 322 along one side of the insulative distal member 372 may be selected to provide pacing at a desired site that achieves the lowest pacing capture threshold due to the relative location of the electrodes 322 to the atrial tissue being paced.

In other instances, the distal-facing surface 338 may be oriented at an angle relative to the adjacent endocardial surface depending on the positioning and orientation at which the tissue-piercing electrode assembly 312 enters the cardiac tissue. In this situation, one or more of the non-tissue piercing electrodes 322 may be positioned in closer contact with the adjacent endocardial tissue than other non-tissue piercing electrodes 322, which may be angled away from the endocardial surface. By providing multiple non-tissue piercing electrodes along the periphery of the insulative distal member 372, the angle of the tissue-piercing electrode assembly 312 and the housing distal end region 332 relative to the cardiac surface, e.g., the right atrial endocardial surface, may not be required to be substantially parallel. Anatomical and positional differences may cause the distal-facing surface 338 to be angled or oblique to the endocardial surface, however, multiple non-tissue piercing electrodes 322 distributed along the periphery of the insulative distal member 372 increase the likelihood of good contact between one or more electrodes 322 and the adjacent cardiac tissue to promote acceptable pacing thresholds and reliable cardiac event sensing using at least a subset of multiple electrodes 322. Contact or fixation circumferentially along the entire periphery of the insulative distal member 372 may not be required.

The non-tissue piercing electrodes 322 are shown to each include a first portion 322a extending along the distal-facing surface 338 and a second portion 322b extending along the circumferential surface 339. The first portion 322a and the second portion 722b may be continuous exposed surfaces such that the active electrode surface wraps around a peripheral edge 376 of the insulative distal member 372 that joins the distal facing surface 338 and the circumferential surface 339. The non-tissue piercing electrodes 322 may include one or more of the electrodes 322 along the distal-facing surface 338, one or more electrodes along the circumferential surface 339, one or more electrodes each extending along both of the distal-facing surface 338 and the circumferential surface 339, or any combination thereof. The exposed surface of each of the non-tissue piercing electrodes 322 may be flush with respective distal-facing surfaces 338 and/or circumferential surfaces. In other examples, each of the non-tissue piercing electrodes 322 may have a raised surface that protrudes from the insulative distal member 372. Any raised surface of the electrodes 322, however, may define a smooth or rounded, non-tissue piercing surface.

The distal fixation and electrode assembly 336 may seal the distal end region of the housing 330 and may provide a foundation on which the electrodes 322 are mounted. The electrodes 322 may be referred to as housing-based electrodes. The electrodes 322 may not be not carried by a shaft or other extension that extends the active electrode portion away from the housing 330, like the distal tip electrode 342 residing at the distal tip of the helical shaft 340 extending away from the housing 330. Other examples of non-tissue piercing electrodes presented herein that are coupled to a distal-facing surface and/or a circumferential surface of an insulative distal member include the distal housing-based electrode 22 as described herein with respect to device 10 of FIG. 4, the distal housing-based electrode extending circumferentially around the assembly 36 as described herein with respect to device 10 of FIG. 4, button electrodes, other housing-based electrodes, and other circumferential ring electrodes. Any non-tissue piercing electrodes directly coupled to a distal insulative member, peripherally to a central tissue-piercing electrode, may be provided to function individually, collectively, or in any combination as a cathode electrode for delivering pacing pulses to adjacent cardiac tissue. When a ring electrode, such as the distal housing-based electrode 22 and/or a circumferential ring electrode, is provided, portions of the ring electrode may be electrically insulated by a coating to provide multiple distributed non-tissue piercing electrodes along the distal-facing surface and/or the circumferential surface of the insulative distal member.

The non-tissue piercing electrodes 322 and other examples listed above are expected to provide more reliable and effective atrial pacing and sensing than a tissue-piercing electrode provided along the distal fixation and electrode assembly 336. The atrial chamber walls are relatively thin compared to ventricular chamber walls. A tissue-piercing atrial cathode electrode may extend too deep within the atrial tissue leading to inadvertent sustained or intermittent capture of ventricular tissue. A tissue-piercing atrial cathode electrode may lead to interference with sensing atrial signals due to ventricular signals having a larger signal strength in the cardiac electrical signal received via tissue-piercing atrial cathode electrodes that are in closer physical proximity to the ventricular tissue. The tissue-piercing electrode assembly 312 may be securely anchored into ventricular tissue for stabilizing the implant position of the device 310 and providing reasonable certainty that the tip electrode 342 is sensing and pacing in ventricular tissue while the non-tissue piercing electrodes 322 are reliably pacing and sensing in the atrium. When the device 310 is implanted in the target implant region 4, e.g., as shown in FIGS. 1-2 with respect to device 10, the tip electrode 342 may reach left ventricular tissue for pacing of the left ventricle while the non-tissue piercing electrodes 322 provide pacing and sensing in the right atrium. The tissue-piercing electrode assembly 312 may be in the range of about 4 to about 8 mm in length from the distal-facing surface 338 to reach left ventricular tissue. In some instances, the device 310 may achieve four-chamber pacing by delivering atrial pacing pulses from the atrial pacing circuit 83 via the non-tissue piercing electrodes 322 in the target implant region 4 to achieve bi-atrial (right and left atrial) capture and by delivering ventricular pacing pulses from a ventricular pacing circuit via the tip electrode 342 advanced into ventricular tissue from the target implant region 4 to achieve biventricular (right and left ventricular) capture.

Figure 6:
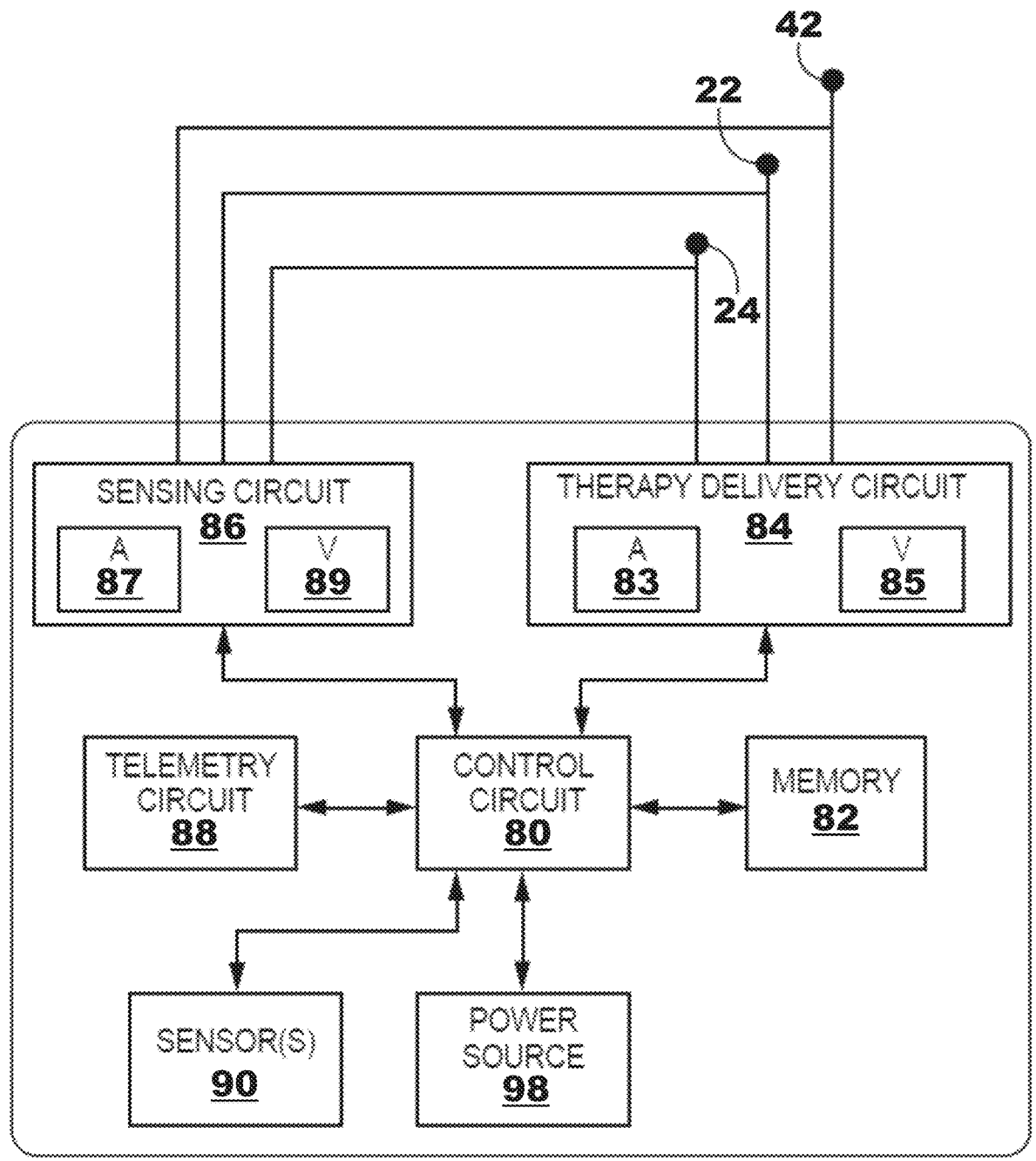
FIG. 6 is a block diagram of illustrative circuitry that may be enclosed within the housing of the medical devices of FIGS. 1-2 and 4-5, for example, to provide the functionality and therapy described herein.

FIG. 6 is a block diagram of circuitry that may be enclosed within the housings 30, 330 of the devices 10, 310 to provide the functions of sensing cardiac signals, determining capture, and/or delivering pacing therapy according to one example or within the housings of any other medical devices described herein. The separate medical device 50 as shown in FIG. 1 may include some or all the same components, which may be configured in a similar manner. The electronic circuitry enclosed within the housings 30, 330 may include software, firmware, and hardware that cooperatively monitor atrial and ventricular electrical cardiac signals, determine whether cardiac system capture has occurred, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the devices 10, 310 includes one or more sensors 90 for producing signals that are correlated to one or more physiological functions, states, or conditions of the patient. For example, the sensor(s) 90 may include a patient activity sensor, for use in determining a need for pacing therapy and/or controlling a pacing rate. Further, for example, the sensor(s) 90 may include an inertial measurement unit (e.g., accelerometer) to measure motion. Further, for example, the sensor(s) 90 may include an acoustic sensor to monitor cardiac sounds. Still further, for example, the sensor(s) 90 may include a patient activity sensor, which may include an accelerometer. An increase in the metabolic demand of the patient due to increased activity as indicated by the patient activity sensor may be determined using the patient activity sensor. In other words, the devices 10, 310 may include other sensors 90 for sensing signals from the patient for use in determining whether to deliver and/or controlling electrical stimulation therapies delivered by the therapy delivery circuit 84.

The power source 98 may provide power to the circuitry of the devices 10, 310 including each of the components 80, 82, 84, 86, 88, 90 as needed. The power source 98 may include one or more energy storage devices, such as one or more rechargeable or non-rechargeable batteries. The connections (not shown) between the power source 98 and each of the components 80, 82, 84, 86, 88, 90 may be understood from the general block diagram illustrated to one of ordinary skill in the art. For example, the power source 98 may be coupled to one or more charging circuits included in the therapy delivery circuit 84 for providing the power used to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown represent functionality included in the devices 10, 310 and may include any discrete and/or integrated electronic circuit components that implement analog, and/or digital circuits capable of producing the functions attributed to the medical devices 10, 310 described herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to determine cardiac conduction system capture and/or perform a single, dual, or triple chamber calibrated pacing therapy (e.g., single or multiple chamber pacing), or other cardiac therapy functions (e.g., sensing or delivering therapy), attributed to the devices 10, 310. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrodes 42, 342, the distal housing-based electrodes 22, 322, and the proximal housing-based electrodes 24, 324 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrodes 22, 322 and the proximal housing-based electrodes 24, 324 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrodes 42, 324 and the proximal housing-based electrodes 24, 324 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (A-V) pacing interval. If an R-wave is sensed before the A-V pacing interval expires, the ventricular pacing pulse may be inhibited. If the A-V pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the devices 10, 310 may be configured to deliver a variety of pacing therapies including bradycardia pacing, cardiac resynchronization therapy, post-shock pacing, and/or tachycardia-related therapy, such as ATP, among others. For example, the devices 10, 310 may be configured to detect non-sinus tachycardia and deliver ATP. The control circuit 80 may determine cardiac event time intervals, e.g., P-P intervals between consecutive P-wave sensed event signals received from the atrial sensing channel 87, R-R intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83, 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83, 85. The tip electrodes 42, 342 and the proximal housing-based electrodes 24, 324 may be coupled to the ventricular pacing circuit 85 as a bipolar cathode and anode pair for delivering ventricular pacing pulses, e.g., upon expiration of an A-V or V-V pacing interval set by the control circuit 80 for providing atrial-synchronized ventricular pacing and a basic lower ventricular pacing rate.

The atrial pacing circuit 83 may be coupled to the distal housing-based electrodes 22, 322 and the proximal housing-based electrodes 24, 324 to deliver atrial pacing pulses. The control circuit 80 may set one or more atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an A-V pacing interval in response to a delivered atrial pacing pulse to provide synchronized multiple chamber pacing (e.g., dual or triple chamber pacing).

Charging of a holding capacitor of the atrial or ventricular pacing circuit 83, 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device, such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

Figure 7:
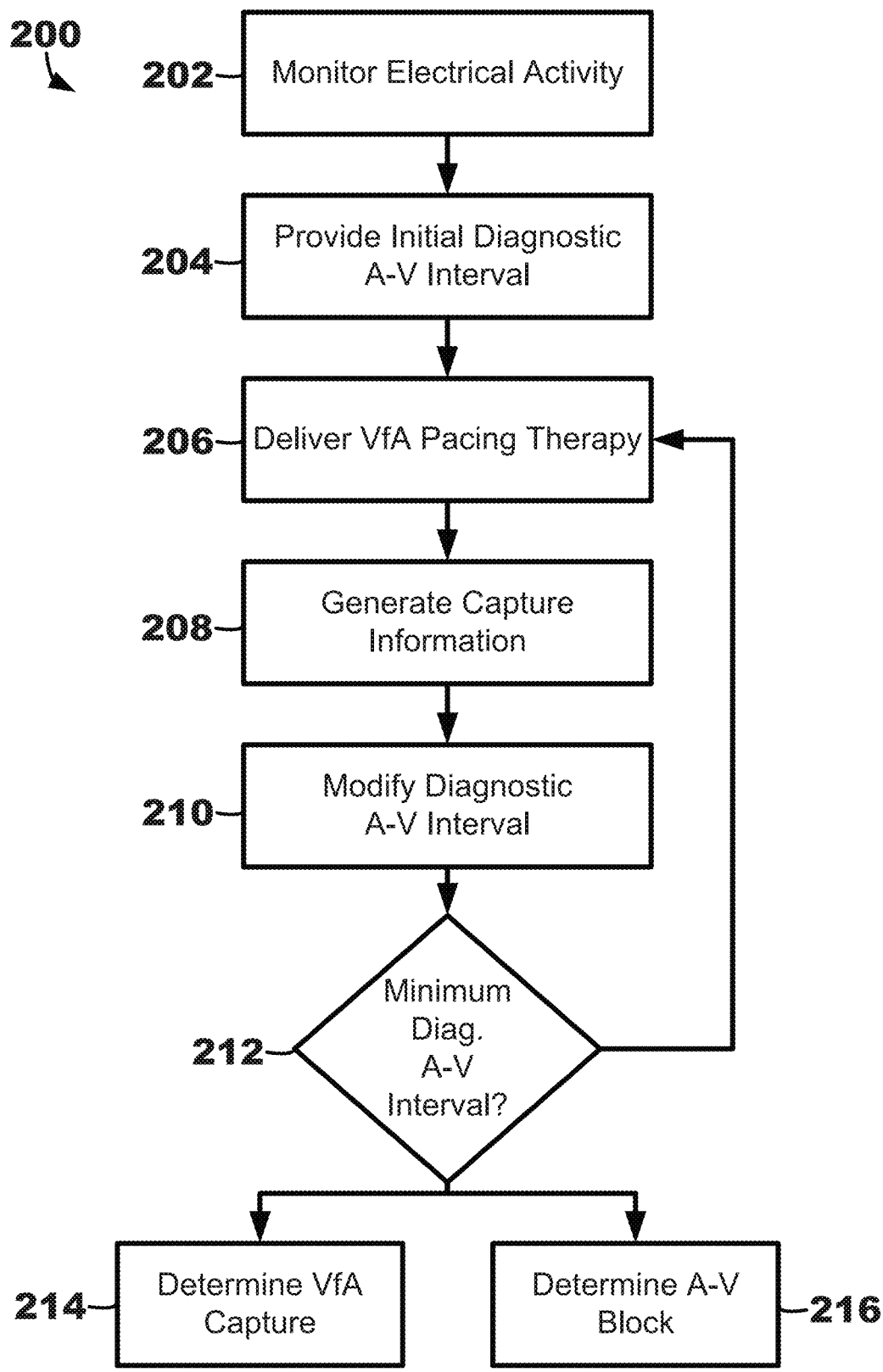
FIG. 7 is a block diagram of an illustrative method of determining cardiac conduction system capture.

The illustrative systems, methods, and devices described herein may be used, or configured, to determine whether the cardiac conduction system or other cardiac tissue such as, e.g., myocardial tissue, is captured by VfA cardiac pacing therapy. An illustrative method 200 of determining cardiac conduction system capture is depicted in FIG. 7. Generally, it may be described that the illustrative method 200 may be used to analyze electrical activity, either internally from cardiac tissue or externally (e.g., from the torso of the patient), adjust the VfA cardiac pacing therapy using a variety of diagnostic pacing settings, and then determine whether or not the VfA cardiac pacing therapy has captured (e.g., is pacing) the cardiac conduction system of the patient based on the monitored electrical activity. Additionally, the method 200 may be able to determine whether the patient has A-V block based on the monitored electrical activity.

As shown, the method 200 may include monitoring electrical activity 202. The electrical activity may be measured externally from the patient or internally form the patient. In other words, the electrical activity may be measured from tissue outside the patient's body (e.g., skin) or from tissue (e.g., heart tissue) inside the patient's body.

Figure 9:
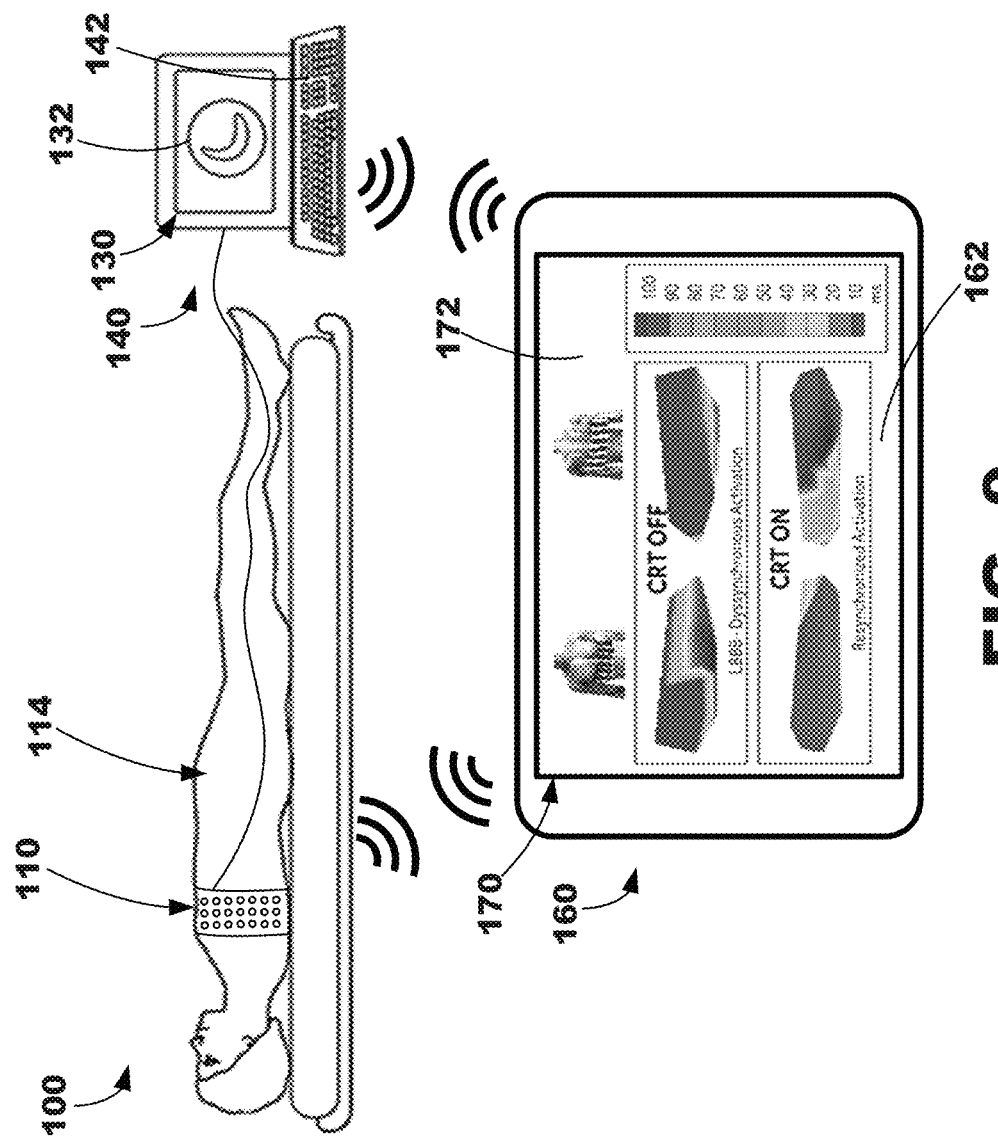
FIG. 9 is a diagram of an illustrative system including electrode apparatus, display apparatus, and computing apparatus.
Figure 10:
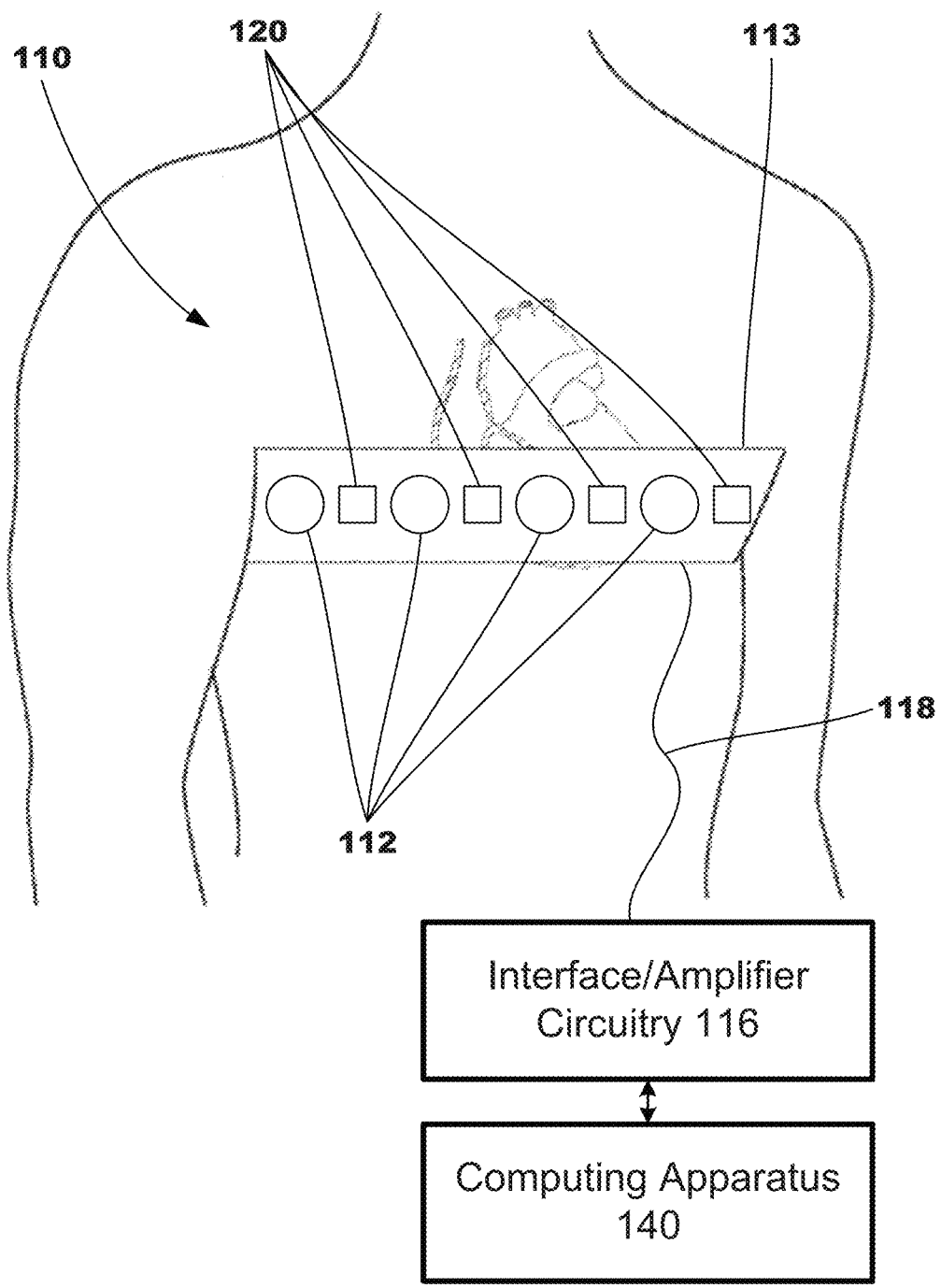
FIGS. 10-11 are diagrams of illustrative external electrode apparatus for measuring torso-surface potentials.
Figure 11:
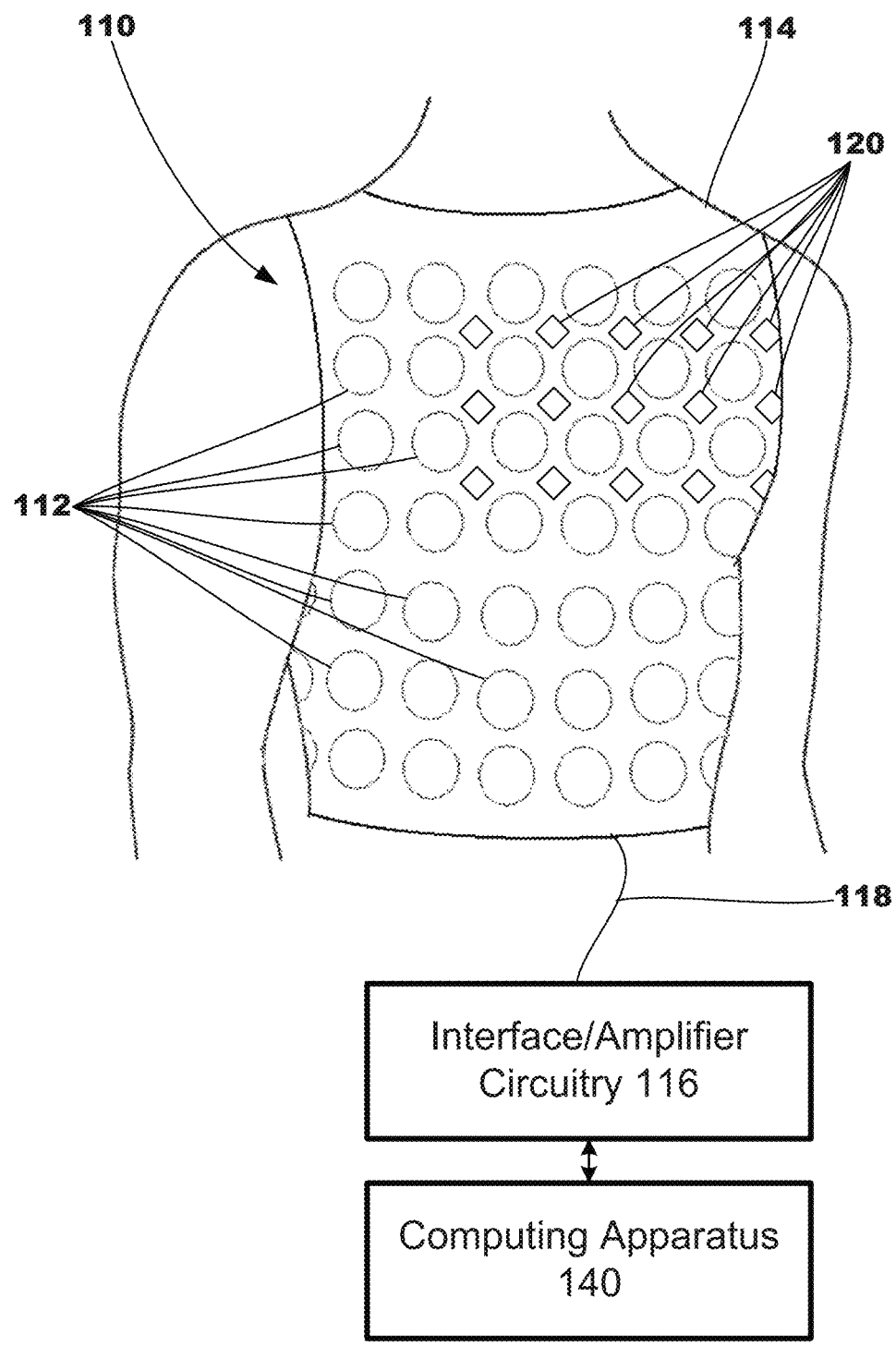

For example, the method 200 may include monitoring, or measuring, electrical activity using a plurality of external electrodes such as, e.g., shown and described with respect to FIGS. 9-11. More specifically, for instance, the plurality of external electrodes may be similar to the external electrodes provided by the electrode apparatus 110 as described herein with respect to FIGS. 9-11. In one embodiment, the plurality of external electrodes may be part, or incorporated into, a vest or band that is located about a patient's torso. More specifically, the plurality of electrodes may be described as being surface electrodes positioned in an array configured to be located proximate the skin of the torso of a patient. It may be described that when using a plurality of external electrodes, the monitoring process 202 may provide a plurality electrocardiograms (ECGs), signals representative of the depolarization and repolarization of the patient's heart, and/or a plurality of activation times.

Further, for example, the method 200 may include monitoring, or measuring, electrical activity using one or more implantable electrodes such as, e.g., shown and described with respect to FIGS. 1-6. In one or more embodiments, the implantable electrodes may be positioned inside of one or more chambers of the patient's heart such as one or more of the right atrium, left atrium, right ventricle, and left ventricle. In one or more embodiments, the implantable electrodes may be positioned proximate cardiac tissue such as one or more of the myocardium, endocardium, and the pericardial space. The electrical activity may be provided as one or more electrograms (EGMs) or electrical signals of the depolarization and repolarization of the patient's heart.

VfA cardiac therapy may be delivered to the left ventricle using an A-V delay or interval, which is the time period between an atrial event (e.g., paced depolarization or intrinsic depolarization) and the left ventricular pace. It is to be understood that the terms A-V delay and A-V interval are used interchangeably in the described provided herein. In other words, A-V interval is the same as A-V delay, and vice versa.

The method 200 may further include providing an initial diagnostic A-V interval 204. The diagnostic A-V interval may be described as being a selected, or determined, interval configured for use in the processes described herein with respect to illustrative method 200 in order to determine whether the VfA cardiac therapy has captured the cardiac conduction system and/or the patient has A-V block.

The initial diagnostic A-V interval may less than the patient's intrinsic A-V interval. The patient's intrinsic A-V interval is the time period between an atrial event (e.g., paced depolarization or intrinsic depolarization) and an intrinsic, or natural, left ventricular depolarization. The initial diagnostic A-V interval may be determined based on the patient's intrinsic A-V interval. For example, the patient's intrinsic A-V interval may be measured, or sensed, and then an initial diagnostic A-V interval may be generated, or calculated, based on the patient's intrinsic A-V interval.

In one embodiment, the initial diagnostic A-V interval may be a selected percentage of the patient's intrinsic A-V interval. The selected percentage may be between about 50% and about 90% of the patient's intrinsic A-V interval. In at least one embodiment, the selected percentage may be 70% of the patient's intrinsic A-V interval. For example, if patient's intrinsic A-V delay is 150 ms and the selected percentage is 70%, then the new, modified, diagnostic A-V interval may be set to 105 ms.

In another embodiment, the initial diagnostic A-V interval may be a selected time period less than the patient's intrinsic A-V interval. The selected time period may be between about 20 milliseconds (ms) and about 50 ms less than the patient's intrinsic A-V interval. For example, if patient's intrinsic A-V delay is 160 ms and the selected time period is 30 ms, then the new, modified diagnostic A-V interval intrinsic A-V interval may be set to 130 ms.

VfA pacing therapy may be delivered 206 using, or according to, the initial diagnostic A-V interval. It is to be understood that the during, or simultaneous with, delivery of VfA pacing therapy 206, the illustrative method 200 may continue monitoring, or collecting, electrical activity 202.

More specifically, the VfA cardiac therapy 206 using the initial diagnostic A-V interval or delay may be delivered by at least one electrode configured to electrically stimulate (e.g., depolarize, pace, etc.) the patient's left ventricle after either an atrial sense or atrial pace in left ventricular-only pacing or the patient's left ventricle and right ventricle after either an atrial sense or atrial pace in biventricular pacing. In some embodiments, the VfA pacing therapy using the initial diagnostic A-V interval may be delivered for a therapy period of time between about 5 seconds and about 30 seconds. In some embodiments, the VfA pacing therapy using the initial diagnostic A-V interval may be delivered for a therapy number of cardiac cycles between about 5 cardiac cycles and about 30 cardiac cycles.

In at least one embodiment, each of the electrodes may be coupled to one or more leads implanted in, or proximate to, the patient's heart. Further, in at least one embodiment, the cardiac therapy 206 may be delivered by a lead-less electrode such as shown and described with respect to FIGS. 1-6. Although such the systems and devices of FIGS. 1-6 are leadless, it is to be understood that the illustrative systems, devices, and methods described herein may be used with any type of cardiac pacing systems including a lead, two leads, three leads, and more than three leads. Further, in at least one embodiment, an illustrative device may be implanted in the patient's right atrium and one or more "leadlets," or short leads, may extend from the device to another portion or region of cardiac tissue such as, e.g., another chamber (e.g., right ventricle), a different septal wall (e.g., atrial septum), etc. As described herein, although the cardiac therapy delivery may be described as being invasive, some of the illustrative systems, devices, and methods such as those described with respect to the FIGS. 9-11 may be described as being noninvasive.

Further, one or more illustrative cardiac therapies may utilize an leaded or leadless implantable cardiac device that includes a tissue-piercing electrode implantable from the triangle of Koch region of the right atrium through the right atrial endocardium and central fibrous body to deliver cardiac therapy to or sense electrical activity of the left ventricle in the basal and/or septal region of the left ventricular myocardium of a patient's heart as described in U.S. Provisional Patent Application Ser. No. 62/647,414 entitled "VfA CARDIAC THERAPY" and filed on Mar. 23, 2018, and U.S. Provisional Patent Application Ser. No. 62/725,763 entitled "ADAPTIVE VfA CARDIAC THERAPY" and filed on Aug. 31, 2018, each of which is incorporated by reference herein in their entireties.

The monitored electrical activity may be used to generate capture information 208 that may be further used to determine capture of the cardiac conduction system by the VfA cardiac therapy and, optionally, determine whether the patient has A-V block. It may be described that capture of the cardiac conduction system, as opposed to capture of other cardiac tissue, means that the pacing electrode of the VfA cardiac therapy that is intended to depolarize at least the left ventricle is delivering the electrical pace to the results in a fast propagation of electrical activation with a low degree of electrical heterogeneity of activation across the ventricles. The cardiac conduction system includes a specialized network of cells comprising the left and right bundle branches as well as a highly branched network of specialized Purkinje fibers that aids in rapid propagation of electrical activation across the ventricles and leads to a very synchronized action of the heart. The cardiac conduction system is part of the natural pathway of electrical conduction that comes down to the ventricles via the A-V node. However, during activation from conventional ventricular pacing, electrical activation propagates from one myocardial cell to another myocardial cell (also referred to as "cell-to-cell") and is slower and asynchronous without any involvement of the specialized cardiac conduction system.

In one embodiment, the capture information 208 may include electrical heterogeneity information (EHI) generated from the monitored electrical activity during the VfA pacing therapy at the initial A-V diagnostic interval, as well as subsequent A-V diagnostic intervals as will be described further herein. The EHI may be described as information, or data, representative of at least one of mechanical cardiac functionality and electrical cardiac functionality. The EHI and other cardiac therapy information may be described in U.S. Provisional Patent Application No. 61/834,133 entitled "METRICS OF ELECTRICAL DYSSYNCHRONY AND ELECTRICAL ACTIVATION PATTERNS FROM SURFACE ECG ELECTRODES" and filed on Jun. 12, 2013, which is hereby incorporated by reference it its entirety.

Electrical heterogeneity information (e.g., data) may be defined as information indicative of at least one of mechanical synchrony or dyssynchrony of the heart and/or electrical synchrony or dyssynchrony of the heart. In other words, electrical heterogeneity information may represent a surrogate of actual mechanical and/or electrical functionality of a patient's heart. In at least one embodiment, relative changes in electrical heterogeneity information (e.g., from baseline heterogeneity information to therapy heterogeneity information, from a first set of heterogeneity information to a second set of therapy heterogeneity information, etc.) may be used to determine a surrogate value representative of the changes in hemodynamic response (e.g., acute changes in LV pressure gradients). The left ventricular pressure may be typically monitored invasively with a pressure sensor located in the left ventricular of a patient's heart. As such, the use of electrical heterogeneity information to determine a surrogate value representative of the left ventricular pressure may avoid invasive monitoring using a left ventricular pressure sensor.

In at least one embodiment, the electrical heterogeneity information may include a standard deviation of ventricular activation times measured using some or all of the external electrodes, e.g., of the electrode apparatus 110 described herein with respect FIGS. 9-11. Further, local, or regional, electrical heterogeneity information may include standard deviations and/or averages of activation times measured using electrodes located in certain anatomic areas of the torso. For example, external electrodes on the left side of the torso of a patient may be used to compute local, or regional, left electrical heterogeneity information.

The electrical heterogeneity information may be generated using one or more various systems and/or methods. For example, electrical heterogeneity information may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

Electrical heterogeneity information may include one or more metrics or indices. For example, one of the metrics, or indices, of electrical heterogeneity may be a standard deviation of activation times (SDAT) measured using some or all of the electrodes on the surface of the torso of a patient. In some examples, the SDAT may be calculated using the estimated cardiac activation times over the surface of a model heart.

Another metric, or index, of electrical heterogeneity may be a left standard deviation of surrogate electrical activation times (LVED) monitored by external electrodes located proximate the left side of a patient. Further, another metric, or index, of electrical heterogeneity may include an average of surrogate electrical activation times (LVAT) monitored by external electrodes located proximate the left side of a patient. The LVED and LVAT may be determined (e.g., calculated, computed, etc.) from electrical activity measured only by electrodes proximate the left side of the patient, which may be referred to as "left" electrodes. The left electrodes may be defined as any surface electrodes located proximate the left ventricle, which includes region to left of the patient's sternum and spine. In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left and right sides of the heart as determined using imaging apparatus (e.g., x-ray, fluoroscopy, etc.).

Another illustrative metric, or index, of dyssynchrony may be a range of activation times (RAT) that may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

Another illustrative metric, or index, of electrical heterogeneity information may include estimates of a percentage of surface electrodes located within a particular region of interest for the torso or heart whose associated activation times are greater than a certain percentile, such as, for example the 70th percentile, of measured QRS complex duration or the determined activation times for surface electrodes. The region of interest may, e.g., be a posterior, left anterior, and/or left-ventricular region. The illustrative metric, or index, may be referred to as a percentage of late activation (PLAT). The PLAT may be described as providing an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, the electrical heterogeneity information may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Heterogeneity information may also include measurements of improved cardiac mechanical function measured by imaging or other systems to track motion of implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZING CRT THERAPY" and published on Apr. 16, 2009, each of which is incorporated herein by reference in its entirety.

In one embodiment, the capture information 208 may include one or more metrics, or indices, of electrogram (EGM) signals data monitored, or measured, directly from cardiac tissue and/or include one or more metrics, or indices, of electrocardiogram (ECG) signals monitored, or measured, indirectly from a patient torso. For example, the QRS morphology, QRS, duration, timing intervals between fiducial points on a ventricular EGM during depolarization (for example difference between the timing of minimum amplitude and maximum amplitude), the peak-to-peak amplitude, amplitudes of slopes or derivatives, and a combination of two or more of these metrics or characteristics from one or both of the EGM and ECG signals may be generated and recorded.

The illustrative method 200 may further including modifying, or adjusting, the A-V diagnostic interval 210 after electrical activity has been monitored 202 during delivery of VfA pacing therapy 206 at the previous diagnostic A-V interval (which, in the first iteration, would be the initial diagnostic A-V interval provided by process 204).

In one embodiment, the A-V diagnostic interval 210 may be modified by decreasing the A-V diagnostic interval by a selected amount. For example, the selected amount may be between about 5 ms and about 25 ms. In one or more embodiments, the selected amount may be greater than or equal to about 5 ms, greater than or equal to about 7 ms, greater than or equal to about 10 ms, greater than or equal to about 12 ms, greater than or equal to about 15 ms, etc. and/or less than or equal to about 30 ms, less than or equal to about 25 ms, less than or equal to about 20 ms, less than or equal to about 17 ms, etc. Thus, if the previous diagnostic A-V interval is 140 ms, and the selected amount is 20 ms, then the modified, or adjusted, A-V diagnostic interval would be 120 ms.

In one embodiment, the A-V diagnostic interval 210 may be modified by decreasing the A-V diagnostic interval by a selected percentage. For example, the selected percentage may be between about 2% ms and about 20% ms. In one or more embodiments, the selected percentage may be greater than or equal to about 2%, greater than or equal to about 5%, greater than or equal to about 7%, etc. and/or less than or equal to about 15%, less than or equal to about 12%, less than or equal to about 10%, etc. Thus, if the previous diagnostic A-V interval is 150 ms, and the selected percentage is 10%, then the modified, or adjusted, A-V diagnostic interval would be 135 ms.

The method 200 may then check whether the modified diagnostic A-V interval is less than a minimum value 212. The minimum value 212 may be between about 40 ms and about 70 ms. In one embodiment, the minimum value 212 is 60 ms. If the modified diagnostic A-V interval is less than the minimum value 212, then the method 200 may proceed to determining whether the VfA pacing therapy has captured the cardiac conduction system 214 and/or determining whether the patient has A-V block 216 as will be described further herein.

If the modified diagnostic A-V interval is not less than a minimum value 212, then the method 200 may return to delivering VfA pacing therapy 206 according to the modified diagnostic A-V interval, generating capture information 208 using the monitored electrical activity 202 during such VfA pacing therapy 208, and then modifying the diagnostic A-V interval 210. The method 200 may continue in this loop until the modified diagnostic A-V interval is less than the minimum value 212.

Thus, the method 200 may be described as modifying the diagnostic A-V interval 210 to be a plurality of different diagnostic A-V intervals, each less than the patient's intrinsic A-V interval, and monitoring electrical activity 202 during each of the plurality of different diagnostic A-V intervals that, in turn, may be used to generate capture information 208. The method 200 may stop, or cease, delivery of the VfA pacing therapy using the diagnostic A-V interval when the diagnostic A-V interval is modified, or decreased, equal to or below the minimum value 212. In other words, it may be described that the diagnostic A-V interval may be "swept" from the initial diagnostic A-V interval to a minimum diagnostic A-V interval, and capture data may be collected during the "sweep."

The method 200 may then utilize one or both of the monitored electrical activity 202 measured during the plurality of different diagnostic A-V intervals and the generated capture information 208 from such monitored electrical activity to determine whether the VfA pacing therapy has captured the cardiac conduction system 214 and/or determine whether the patient has A-V block 216 as will be described further herein.

Determining whether the VfA pacing therapy has captured the cardiac conduction system 214 may be performed using various processes and various capture information. For example, capture information including dyssynchrony information such as, e.g., EHI, may be utilized. Graphs of dyssynchrony over decreasing diagnostic A-V intervals depicting various scenarios of cardiac conduction system capture, no cardiac conduction system capture, and A-V block are depicted in FIGS. 8A-8C.

Figure 8A:
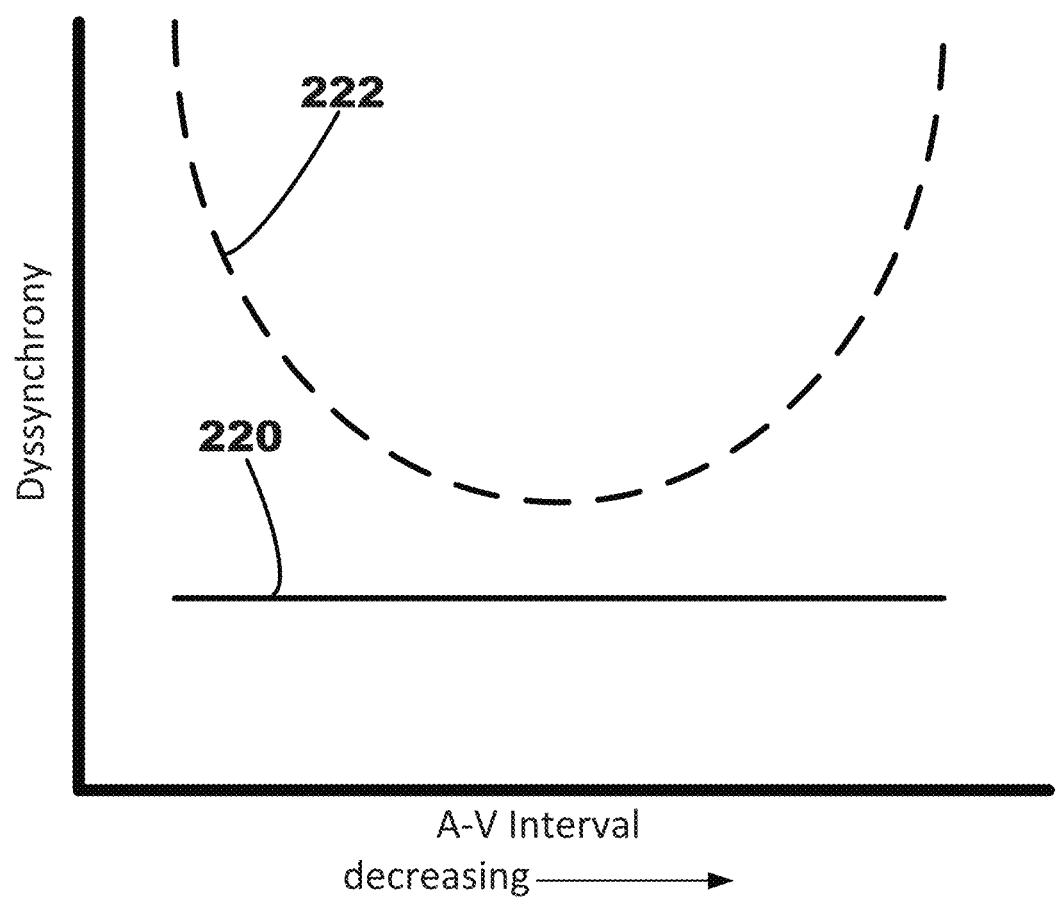
FIGS. 8A-8C are graphs of dyssynchrony over decreasing A-V delays, or intervals, depicting various scenarios of cardiac conduction system capture, no cardiac conduction system capture, and A-V block.
Figure 8B:
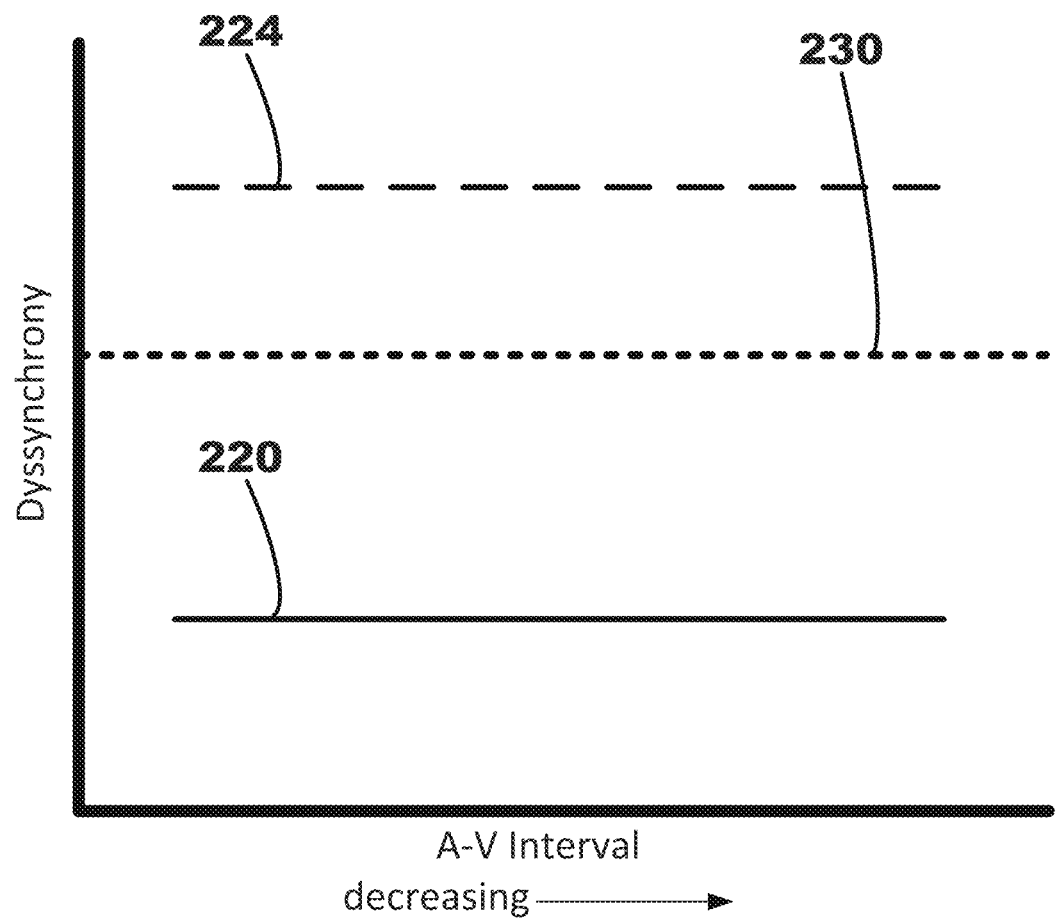
Figure 8C:
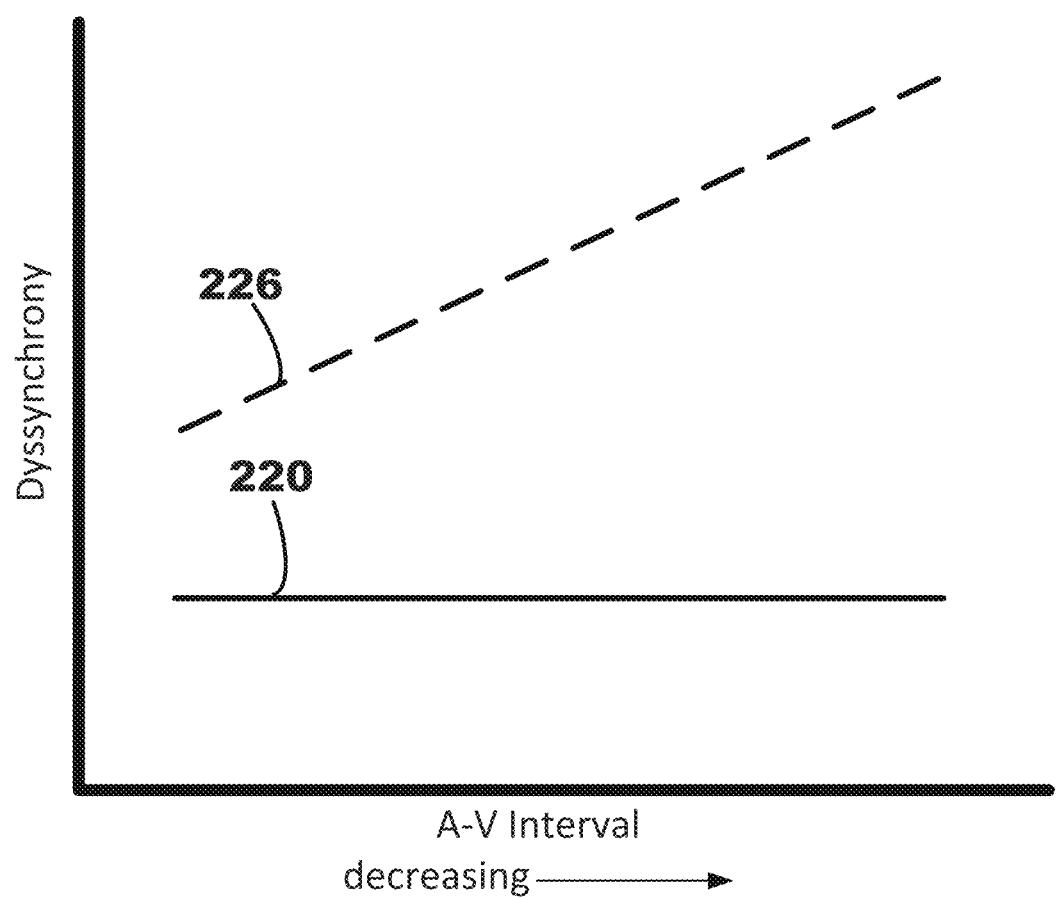

Two different sets of dyssynchrony information are depicted in FIG. 8A. The first set of dyssynchrony information 220 indicates successful capture of the cardiac conduction system while the second set of dyssynchrony information 222 indicates no, or unsuccessful, capture of the cardiac conduction system. As shown in FIG. 8A, as the diagnostic A-V interval decreases (i.e., moving rightward along the X-axis) the first set of dyssynchrony information 220 indicating successful cardiac conduction system capture does not increase or decrease—instead, the first set of dyssynchrony information 220 stays relatively constant such as, for example, within a certain predefined tolerance (e.g., +/−5%, +/−10%, +/−3 ms, +/−5 ms etc.). No change of dyssynchrony over a decreasing diagnostic A-V interval may indicate successful cardiac conduction system capture.

Conversely, as the diagnostic A-V interval decreases, the second set of dyssynchrony information 222 indicating no, or unsuccessful, capture of the cardiac conduction system decreases and then subsequently increases. In brief, the second set of dyssynchrony information 222 changes over time. Change of dyssynchrony over a decreasing diagnostic A-V interval may indicate unsuccessful, or no, cardiac conduction system capture.

Thus, change of dyssynchrony may be determined by increasing electrical heterogeneity or dyssynchrony during pacing at shorter A-V intervals without capturing conduction system, as the entire activation of the heart would take place by means of cell-to-cell propagation, which is much slower. In some cases, when there is considerable local tissue latency (e.g., measured by interval between delivery of pacing and onset of QRS), change of dyssynchrony may be determined by reduction of electrical dyssynchrony during pacing at shorter A-V intervals without capturing the conduction system.

Thus, the illustrative method 200 may determine that the VfA pacing therapy has not captured the cardiac conduction system 214 if the dyssynchrony information such as, e.g., EHI, changes as the diagnostic A-V interval decreases. Further, and likewise, the illustrative method 200 may determine that the VfA pacing therapy has captured the cardiac conduction system 214 if the dyssynchrony information such as, e.g., EHI, remains relatively constant as the diagnostic A-V interval decreases.

Two different sets of dyssynchrony information are depicted in FIG. 8B, and both the first set of dyssynchrony information 220 and the second set of dyssynchrony information 224 indicate successful capture of the cardiac conduction system because, e.g., they do not increase or decrease, both sets 220, 224 stay relatively constant, etc. However, the second set of dyssynchrony information 224 is above a threshold value 230, which may indicate A-V block. If the dyssynchrony metric being utilized is standard deviation of activation times (SDAT), the threshold value may be between about 20 ms and 25 ms.

Thus, the illustrative method 200 may determine that the patient has A-V block if the dyssynchrony information remains relatively constant and is above a selected threshold over a plurality of different diagnostic A-V intervals (e.g., as the diagnostic A-V interval decreases).

Two different sets of dyssynchrony information are depicted in FIG. 8C. The first set of dyssynchrony information 220 indicates successful capture of the cardiac conduction system while the second set of dyssynchrony information 226 indicates no, or unsuccessful, capture of the cardiac conduction system. As shown in FIG. 8C, as the diagnostic A-V interval decreases (i.e., moving rightward along the X-axis) the first set of dyssynchrony information 220 indicating successful cardiac conduction system capture does not increase or decrease—instead, the first set of dyssynchrony information 220 stays relatively constant. As before, no change of dyssynchrony over a decreasing diagnostic A-V interval may indicate successful cardiac conduction system capture.

Conversely, as the diagnostic A-V interval decreases, the second set of dyssynchrony information 226 indicating no, or unsuccessful, capture of the cardiac conduction system steadily increases. In brief, the second set of dyssynchrony information 226 changes over time. Change of dyssynchrony over a decreasing diagnostic A-V interval may indicate unsuccessful, or no, cardiac conduction system capture.

Determining whether the VfA pacing therapy has captured the cardiac conduction system 214 may be performed using various processes analyze and evaluate EGM, ECG signals, and/or portions thereof. For example, capture information may include a QRS segment in an EGM and/or ECG signal following a ventricular paced event. One or both of the morphology and duration may be compared over the plurality of different diagnostic A-V intervals to determine whether successful capture of the cardiac conduction system by the VfA pacing therapy has occurred.

In one embodiment, a morphology template of a QRS signal segment following a ventricular pacing event from the time of delivery of pacing to a certain predefined time interval (e.g., 250 ms after delivery of an atrial pace) may be stored during pacing at a certain diagnostic A-V interval (e.g., a short AV delay like 60 ms) and morphologic similarity of the QRS segment during pacing at other diagnostic A-V intervals (e.g., longer diagnostic A-V interval like 80 ms, 100 ms, 120 ms, etc.) may be determined based on simple correlation of the QRS signal segments in the same time-window following delivery of pacing. A similarity in morphology may be determined if the correlation coefficient exceeds a certain threshold (e.g., 90%). Other metrics like relative differences may be also used to determine similarity of electrogram morphology or other characteristics. If relative differences are less than a certain threshold (e.g., 5%, 10% etc.), then a match or similarity of characteristics is determined. If QRS signal segments at short A-V pacing intervals are similar (e.g., closely match, within a tolerance level, etc.) to the QRS signal segments at longer AV pacing intervals (e.g., in terms of one or both of QRS morphology and duration), then it may be determined that the VfA pacing therapy has successfully captured one or both of the left ventricle and right ventricle. Conversely, if QRS signal segments at short A-V pacing intervals are different than the QRS signal segments at longer AV pacing intervals (e.g., in terms of one or both of QRS morphology and duration), then it may be determined that the VfA pacing therapy has not successfully captured one or both of the left ventricle and right ventricle.

As described herein, one of the various ways, or processes, to monitor electrical activity during the plurality of different diagnostic A-V delays, and then generate capture information therefrom utilizes a plurality of electrocardiogram (ECG) signals (e.g., torso-surface potentials). The plurality of ECG signals may be measured, or monitored, using a plurality of external electrodes positioned about the surface, or skin, of a patient. The ECG signals may be used to determine cardiac conduction system capture of VfA therapy, e.g., provide by an implantable medical device performing VfA cardiac resynchronization therapy (CRT). As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by to determine cardiac conduction system capture.

Various illustrative systems, methods, and graphical user interfaces may be configured to use electrode apparatus including external electrodes, display apparatus, and computing apparatus to noninvasively assist a user (e.g., a physician) in the evaluation of cardiac conduction system capture and/or the configuration (e.g., optimization) of cardiac therapy. An illustrative system 100 including electrode apparatus 110, computing apparatus 140, and a remote computing device 160 is depicted in FIG. 9.

The electrode apparatus 110 as shown includes a plurality of electrodes incorporated, or included, within a band wrapped around the chest, or torso, of a patient 114. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

The computing apparatus 140 and the remote computing device 160 may each include display apparatus 130, 160, respectively, that may be configured to display and analyze data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the determination of cardiac conduction system capture and detection of A-V block. More specifically, for example, the QRS complex of a single cardiac cycle may be evaluated for one or more metrics such as, e.g., QRS onset, QRS offset, QRS peak, electrical heterogeneity information (EHI), electrical activation times, left ventricular or thoracic standard deviation of electrical activation times (LVED), standard deviation of activation times (SDAT), average left ventricular or thoracic surrogate electrical activation times (LVAT), referenced to earliest activation time, QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, or a tablet computer. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, for determining electrical activation times, for determining whether VfA pacing therapy has captured the cardiac conduction system, for determining whether the patient has A-V block, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of cardiac conduction system capture information, A-V block information, and configuration information related to the cardiac therapy delivered by cardiac therapy apparatus such as, e.g., an implantable medical device.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

The illustrative electrode apparatus 110 may be configured to measure body-surface potentials of a patient 114 and, more particularly, torso-surface potentials of a patient 114. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 114 such that the electrodes 112 surround the patient's heart. As further illustrated, the electrodes 112 may be positioned around the circumference of a patient 114, including the posterior, lateral, posterolateral, anterolateral, and anterior locations of the torso of a patient 114.

The illustrative electrode apparatus 110 may be further configured to measure, or monitor, sounds from at least one or both the patient 114. As shown in FIG. 2, the illustrative electrode apparatus 110 may include a set, or array, of acoustic sensors 120 attached, or coupled, to the strap 113. The strap 113 may be configured to be wrapped around the torso of a patient 114 such that the acoustic sensors 120 surround the patient's heart. As further illustrated, the acoustic sensors 120 may be positioned around the circumference of a patient 114, including the posterior, lateral, posterolateral, anterolateral, and anterior locations of the torso of a patient 114.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to the computing apparatus 140 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 114. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 114. Still further, in other examples, one or both of the electrodes 112 and the acoustic sensors 120 may be part of, or located within, two sections of material or two patches. One of the two patches may be located on the anterior side of the torso of the patient 114 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 114 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 114 across the left side of the patient 114 to the anterior side of the patient 114. Yet still further, in other examples, one or both of the electrodes 112 and the acoustic sensors 120 may be arranged in a curve around the armpit area and may have an electrode/sensor-density that less dense on the right thorax that the other remaining areas.

The electrodes 112 may be configured to surround the heart of the patient 114 and record, or monitor, the electrical signals associated with the depolarization and repolarization of the heart after the signals have propagated through the torso of a patient 114. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 114. Instead, the electrodes 112 and acoustic sensors 120 may be arranged in an array that extends only part of the way or partially around the patient 114. For example, the electrodes 112 and acoustic sensors 120 may be distributed on the anterior, posterior, and left sides of the patient with less or no electrodes and acoustic sensors proximate the right side (including posterior and anterior regions of the right side of the patient).

The computing apparatus 140 may record and analyze the torso-surface potential signals sensed by electrodes 112 and the sound signals sensed by the acoustic sensors 120, which are amplified/conditioned by the interface/amplifier circuitry 116. The computing apparatus 140 may be configured to analyze the electrical signals from the electrodes 112 to provide electrocardiogram (ECG) signals, information, or data from the patient's heart as will be further described herein. The computing apparatus 140 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient.

Further, the electrode apparatus 110 may further include reference electrodes and/or drive electrodes to be, e.g. positioned about the lower torso of the patient 114, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in a Wilson Central Terminal) to get a "true" unipolar signal with less noise from averaging three caudally located reference signals.

FIG. 3 illustrates another illustrative electrode apparatus 110 that includes a plurality of electrodes 112 configured to surround the heart of the patient 114 and record, or monitor, the electrical signals associated with the depolarization and repolarization of the heart after the signals have propagated through the torso of the patient 114 and a plurality of acoustic sensors 120 configured to surround the heart of the patient 114 and record, or monitor, the sound signals associated with the heart after the signals have propagated through the torso of the patient 114. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 114, including, for example, the posterior, lateral, posterolateral, anterolateral, and anterior locations of the torso of a patient 114.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 114. Further, the vest 114 may be marked to assist in determining the location of the electrodes 112 and the acoustic sensors 120 on the surface of the torso of the patient 114. In some examples, there may be about 25 to about 256 electrodes 112 and about 25 to about 256 acoustic sensors 120 distributed around the torso of the patient 114, though other configurations may have more or fewer electrodes 112 and more or fewer acoustic sensors 120.

The illustrative systems and methods may be used to provide noninvasive assistance to a user in the evaluation of a patient's cardiac health and/or evaluation and configuration of cardiac therapy being presently-delivered to the patient (e.g., by an implantable medical device such as a VfA pacing device, by a LVAD, etc.). For example, the illustrative systems and methods may be used to assist a user in determining whether one or more electrodes have successfully captured one or both ventricles for VfA pacing therapy and whether the patient is undergoing A-V block. Further, for example, the illustrative systems and methods may be used to assist a user in the configuration and/or adjustment of one or more cardiac therapy settings such as, e.g., optimization of the A-V interval, or delay, of pacing therapy (e.g., left ventricular-only, or left univentricular, pacing therapy) and the A-V interval, or delay, and the V-V interval, or delay, of pacing therapy (e.g., biventricular pacing therapy).

Further, it is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

The techniques described in this disclosure, including those attributed to the IMD 10, device 50, IMD 310, the computing apparatus 140, and the computing device 160 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all the listed elements or a combination of at least two of the listed elements. The phrases "at least one of," "comprises at least one of," and "one or more of" followed by a list refers to any one of the items in the list and any combination of two or more items in the list.

ILLUSTRATIVE EMBODIMENTS

Embodiment 1

A system comprising:
electrode apparatus comprising a plurality of electrodes to monitor electrical activity from tissue of a patient; and
computing apparatus comprising processing circuitry and coupled to the electrode apparatus and configured to:
monitor electrical activity of the patient's heart using one or more electrodes of the plurality of electrodes during delivery of ventricle from atrium (VfA) pacing therapy at a plurality of diagnostic A-V delays, wherein each of the plurality of diagnostic A-V delays are less than the patient's intrinsic A-V delay; and
determine whether the VfA pacing therapy has captured the cardiac conduction system based on the monitored electrical activity during delivery of VfA pacing therapy at the plurality of diagnostic A-V delays.

Embodiment 2

A method comprising:
monitoring electrical activity of the patient's heart using one or more electrodes of a plurality of electrodes during delivery of ventricle from atrium (VfA) pacing therapy at a plurality of diagnostic A-V delays, wherein each of the plurality of diagnostic A-V delays are less than the patient's intrinsic A-V delay; and
determining whether the VfA pacing therapy has captured the cardiac conduction system based on the monitored electrical activity during delivery of VfA pacing therapy at the plurality of diagnostic A-V delays.

Embodiment 3

An implantable medical device comprising:
a plurality of electrodes comprising:
a right atrial electrode positionable within the right atrium to deliver cardiac therapy to, or sense electrical activity of, the right atrium of a patient's heart, and
a tissue-piercing electrode implantable through the right atrial endocardium and central fibrous body to deliver cardiac therapy to, or sense electrical activity of, the left ventricle of a patient's heart;
a therapy delivery circuit operably coupled to the plurality of electrodes to deliver cardiac therapy to the patient's heart;
a sensing circuit operably coupled to the plurality of electrodes to sense electrical activity of the patient's heart; and
a controller comprising processing circuitry operably coupled to the therapy delivery circuit and the sensing circuit, the controller configured to:
deliver ventricle from atrium (VfA) pacing therapy using at least the tissue-piercing electrode at a plurality of diagnostic A-V delays, wherein each of the plurality of diagnostic A-V delays are less than the patient's intrinsic A-V delay;
monitor electrical activity of the patient's heart using one or more electrodes of the plurality of electrodes during delivery of VfA pacing therapy at the plurality of diagnostic A-V delays; and
determine whether the VfA pacing therapy has captured the cardiac conduction system based on the monitored electrical activity during delivery of VfA pacing therapy at the plurality of diagnostic A-V delays.

Embodiment 4

The system, method, or device as set forth in any of embodiments 1-3, wherein the system further comprises a VfA pacing therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient's heart.

Embodiment 5

The system, method, or device as set forth in any of embodiments 1-4, wherein the longest diagnostic A-V delay of the plurality of diagnostic A-V delays is less than or equal to 70% of the patient's intrinsic A-V delay.

Embodiment 6

The system or method as set forth in any of embodiments 1-2 and 4-5, wherein the plurality of electrodes comprises a plurality of surface electrodes positioned in an array configured to be located proximate skin of a torso of the patient.

Embodiment 7

The system or method or device as set forth in any of embodiments 1-2 and 4-6, wherein the computing apparatus is further configured to execute or the method further comprises generating electrical heterogeneity information (EHI) based on the monitored electrical activity during delivery of VfA pacing therapy at the plurality of diagnostic A-V delays, wherein determining whether the VfA pacing therapy has captured the cardiac conduction system based on the monitored electrical activity during delivery of VfA pacing therapy at the plurality of diagnostic A-V delays comprises determining whether the VfA pacing therapy has captured the cardiac conduction system based on the EHI.

Embodiment 8

The system or method as set forth in any of embodiment 7, wherein delivery of VfA pacing therapy at a plurality of diagnostic A-V delays comprises decreasing the diagnostic A-V delay over time, and wherein determining whether the VfA pacing therapy has captured the cardiac conduction system based on the EHI comprises determining that the VfA pacing therapy has not captured the cardiac conduction system if the EHI changes as the A-V delay decreases.

Embodiment 9

The system or method as set forth in any of embodiments 1-2 and 4-8, wherein the plurality of electrodes comprises one or more implantable electrodes.

Embodiment 10

The system, method, or device as set forth in any of embodiments 1-9, wherein delivery of VfA pacing therapy at a plurality of diagnostic A-V delays comprises decreasing the diagnostic A-V delay over time, and
wherein determining whether the VfA pacing therapy has captured the cardiac conduction system based on the monitored electrical activity during delivery of VfA pacing therapy at the plurality of diagnostic A-V delays comprises determining that the VfA pacing therapy has not captured the cardiac conduction system if one or both of cardiac signal morphology and duration of the monitored electrical activity changes as the present A-V delay decreases.

Embodiment 11

The system, method, or device as set forth in any of embodiments 1-10, wherein the computing apparatus is further configured to determine A-V block based on the monitored electrical activity during delivery of VfA pacing therapy at the plurality of diagnostic A-V delays.

Embodiment 12

The system, method, or device as set forth in embodiment 11, wherein determining A-V block based on the monitored electrical activity during delivery of VfA pacing therapy at the plurality of diagnostic A-V delays determining AV block if:
one or all of dyssynchrony, cardiac signal morphology, and cardiac signal duration of the monitored electrical activity remains consistent as the present A-V delay decreases; and one or all of dyssynchrony, cardiac signal morphology, and cardiac signal duration of the monitored electrical activity are above a selected A-V block threshold.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system comprising:
   electrode apparatus comprising a plurality of electrodes to monitor electrical activity from tissue of a patient; and
   computing apparatus comprising processing circuitry and coupled to the electrode apparatus and configured to:
      receive a patient's intrinsic A-V delay value;
      monitor electrical activity of the patient's heart using one or more electrodes of the plurality of electrodes during delivery of ventricle from atrium (VfA) pacing therapy at a plurality of diagnostic A-V delay values, wherein VfA pacing therapy comprises delivery of pacing therapy to at least the left ventricle of the patient's heart from one or more VfA electrodes implanted through the right atrial endocardium and central fibrous body of the patient's heart, and wherein each of the plurality of diagnostic A-V delay values are less than the patient's intrinsic A-V delay value; and
      determine whether the VfA pacing therapy has successfully captured the cardiac conduction system based on the monitored electrical activity during delivery of VfA pacing therapy at the plurality of diagnostic A-V delay values.

2. The system of claim 1, wherein the system further comprises a VfA pacing therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient's heart.

3. The system of claim 1, wherein the longest diagnostic A-V delay value of the plurality of diagnostic A-V delay values is less than or equal to 70% of the patient's intrinsic A-V delay value.

4. The system of claim 1, wherein the plurality of electrodes comprises a plurality of surface electrodes positioned in an array configured to be located proximate skin of a torso of the patient.

5. The system of claim 1, wherein the computing apparatus is further configured to generate electrical heterogeneity information (EHI) based on the monitored electrical activity during delivery of VfA pacing therapy at the plurality of diagnostic A-V delay values, wherein EHI is indicative of at least one of mechanical synchrony or dyssynchrony of the heart and/or electrical synchrony or dyssynchrony of the heart, wherein determining whether the VfA pacing therapy has successfully captured the cardiac conduction system based on the monitored electrical activity during delivery of VfA pacing therapy at the plurality of diagnostic A-V delay values comprises determining whether the VfA pacing therapy has successfully captured the cardiac conduction system based on the EHI.

6. The system of claim 5, wherein delivery of VfA pacing therapy at a plurality of diagnostic A-V delay values comprises decreasing the diagnostic A-V delay value over time, and
   wherein determining whether the VfA pacing therapy has successfully captured the cardiac conduction system based on the EHI comprises determining that the VfA pacing therapy has not captured the cardiac conduction system if the EHI changes as the A-V delay value decreases.

7. The system of claim 1, wherein the plurality of electrodes comprises one or more implantable electrodes.

8. The system of claim 1, wherein delivery of VfA pacing therapy at a plurality of diagnostic A-V delay values comprises decreasing the diagnostic A-V delay value over time, and
   wherein determining whether the VfA pacing therapy has successfully captured the cardiac conduction system based on the monitored electrical activity during delivery of VfA pacing therapy at the plurality of diagnostic A-V delay values comprises determining that the VfA pacing therapy has not captured the cardiac conduction system if one or both of cardiac signal morphology and duration of the monitored electrical activity changes as the presently applied diagnostic A-V delay value decreases.

9. The system of claim 1, wherein the computing apparatus is further configured to determine A-V block based on the monitored electrical activity during delivery of VfA pacing therapy at the plurality of diagnostic A-V delay values.

10. The system of claim 9, wherein determining A-V block based on the monitored electrical activity during delivery of VfA pacing therapy at the plurality of diagnostic A-V delay values determining AV block if:
    one or all of dyssynchrony, cardiac signal morphology, and cardiac signal duration of the monitored electrical activity remains consistent as the presently applied diagnostic A-V delay value decreases; and
    one or all of a dyssynchrony metric, a cardiac signal morphology metric, and cardiac signal duration of the monitored electrical activity are above a selected A-V block threshold.

11. A method comprising:
    receiving a patient's intrinsic A-V delay value;
    monitoring electrical activity of the patient's heart using one or more electrodes of a plurality of electrodes during delivery of ventricle from atrium (VfA) pacing therapy at a plurality of diagnostic A-V delay values, wherein VfA pacing therapy comprises delivery of pacing therapy to at least the left ventricle of the patient's heart from one or more VfA electrodes implanted through the right atrial endocardium and central fibrous body of the patient's heart, and wherein each of the plurality of diagnostic A-V delay values are less than the patient's intrinsic A-V delay value; and
    determining whether the VfA pacing therapy has successfully captured the cardiac conduction system based on the monitored electrical activity during delivery of VfA pacing therapy at the plurality of diagnostic A-V delay values.

12. The method of claim 11, wherein the delivery of the VfA pacing therapy is performed by a VfA pacing therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient.

13. The method of claim 11, wherein the longest diagnostic A-V delay value of the plurality of diagnostic A-V delay values is less than or equal to 70% of the patient's intrinsic A-V delay value.

14. The method of claim 11, wherein the plurality of electrodes comprises a plurality of surface electrodes positioned in an array configured to be located proximate skin of a torso of the patient.

15. The method of claim 11, further comprising generating electrical heterogeneity information (EHI) based on the monitored electrical activity during delivery of VfA pacing therapy at the plurality of diagnostic A-V delay values, wherein EHI is indicative of at least one of mechanical synchrony or dyssynchrony of the heart and/or electrical synchrony or dyssynchrony of the heart,
wherein determining whether the VfA pacing therapy has successfully captured the cardiac conduction system based on the monitored electrical activity during delivery of VfA pacing therapy at the plurality of diagnostic A-V delay values comprises determining whether the VfA pacing therapy has successfully captured the cardiac conduction system based on the EHI.

16. The method of claim 15, wherein delivery of VfA pacing therapy at a plurality of diagnostic A-V delay values comprises decreasing the diagnostic A-V delay value over time, and
wherein determining whether the VfA pacing therapy has successfully captured the cardiac conduction system based on the EHI comprises determining that the VfA pacing therapy has not captured the cardiac conduction system if the EHI changes as the A-V delay value decreases.

17. The method of claim 11, wherein the plurality of electrodes comprises one or more implantable electrodes.

18. The method of claim 11, wherein delivery of VfA pacing therapy at a plurality of diagnostic A-V delay values comprises decreasing the diagnostic A-V delay value over time, and
wherein determining whether the VfA pacing therapy has successfully captured the cardiac conduction system based on the monitored electrical activity during delivery of VfA pacing therapy at the plurality of diagnostic A-V delay values comprises determining that the VfA pacing therapy has not captured the cardiac conduction system if one or both of cardiac signal morphology and duration of the monitored electrical activity changes as the presently applied diagnostic A-V delay value decreases.

19. The method of claim 11, further comprising determining A-V block based on the monitored electrical activity during delivery of VfA pacing therapy at the plurality of diagnostic A-V delay values.

20. An implantable medical device comprising:
a plurality of electrodes comprising:
a right atrial electrode positionable within the right atrium of a patient's heart to deliver cardiac therapy to, or sense electrical activity of, the right atrium of the patient's heart, and
a tissue-piercing electrode implantable through the right atrial endocardium and central fibrous body of the patient's heart to deliver cardiac therapy to, or sense electrical activity of, the left ventricle of the patient's heart;
a therapy delivery circuit operably coupled to the plurality of electrodes to deliver cardiac therapy to the patient's heart;
a sensing circuit operably coupled to the plurality of electrodes to sense electrical activity of the patient's heart; and
a controller comprising processing circuitry operably coupled to the therapy delivery circuit and the sensing circuit, the controller configured to:
monitor a patient's intrinsic A-V delay value using the plurality of electrodes;
deliver ventricle from atrium (VfA) pacing therapy using at least the tissue-piercing electrode at a plurality of diagnostic A-V delay values, wherein each of the plurality of diagnostic A-V delay values are less than the patient's intrinsic A-V delay value;
monitor electrical activity of the patient's heart using one or more electrodes of the plurality of electrodes during delivery of VfA pacing therapy at the plurality of diagnostic A-V delay values; and
determine whether the VfA pacing therapy has successfully captured the cardiac conduction system based on the monitored electrical activity during delivery of VfA pacing therapy at the plurality of diagnostic A-V delay values.

21. The device of claim 20, wherein the longest diagnostic A-V delay value of the plurality of diagnostic A-V delay values is less than or equal to 70% of the patient's intrinsic A-V delay value.

22. The device of claim 20, wherein delivering VfA pacing therapy at a plurality of diagnostic A-V delay values comprises decreasing the diagnostic A-V delay value over time, and
wherein determining whether the VfA pacing therapy has successfully captured the cardiac conduction system based on the monitored electrical activity during delivery of VfA pacing therapy at the plurality of diagnostic A-V delay values comprises determining that the VfA pacing therapy has not captured the cardiac conduction system if one or both of cardiac signal morphology and duration of the monitored electrical activity changes as the presently applied diagnostic A-V delay value decreases.

23. The device of claim 20, wherein the controller is further configured to determine A-V block based on the monitored electrical activity during delivery of VfA pacing therapy at the plurality of diagnostic A-V delay values.

24. The device of claim 23, wherein determining A-V block based on the monitored electrical activity during delivery of VfA pacing therapy at the plurality of diagnostic A-V delay values determining AV block if:
one or all of dyssynchrony, cardiac signal morphology, and cardiac signal duration of the monitored electrical activity remains consistent as the presently applied diagnostic A-V delay value decreases; and
one or all of a dyssynchrony metric, a cardiac signal morphology metric, and cardiac signal duration of the monitored electrical activity are above a selected A-V block threshold.

* * * * *